United States Patent
Karumbaiah et al.

(10) Patent No.: US 12,090,229 B2
(45) Date of Patent: Sep. 17, 2024

(54) CHONDROITIN SULFATE GLYCOSAMINOGLYCAN HYDROGEL MATRICES FOR THE TREATMENT OF TRAUMATIC BRAIN INJURY

(71) Applicant: UNIVERSITY OF GEORGIA RESEARCH FOUNDATION, INC., Athens, GA (US)

(72) Inventors: Lohitash Karumbaiah, Bogart, GA (US); Leidong Mao, Watkinsville, GA (US); Meghan T. Logun, Marietta, GA (US); Wujun Zhao, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 309 days.

(21) Appl. No.: 17/518,759

(22) Filed: Nov. 4, 2021

(65) Prior Publication Data
US 2022/0125731 A1    Apr. 28, 2022

Related U.S. Application Data

(63) Continuation of application No. 16/322,680, filed as application No. PCT/US2017/044845 on Aug. 1, 2017.

(60) Provisional application No. 62/369,658, filed on Aug. 1, 2016.

(51) Int. Cl.
| | | |
|---|---|---|
| A61K 31/726 | (2006.01) | |
| A61K 9/19 | (2006.01) | |
| A61K 47/69 | (2017.01) | |
| C12M 1/12 | (2006.01) | |
| C12N 5/00 | (2006.01) | |
| G01N 33/50 | (2006.01) | |
| C12M 3/06 | (2006.01) | |

(52) U.S. Cl.
CPC .............. *A61K 9/19* (2013.01); *A61K 31/726* (2013.01); *A61K 47/6903* (2017.08); *C12M 25/02* (2013.01); *C12N 5/0012* (2013.01); *G01N 33/5029* (2013.01); *C12M 23/16* (2013.01)

(58) Field of Classification Search
CPC ................................ A61K 9/19; A61K 31/726
See application file for complete search history.

(56) References Cited

U.S. PATENT DOCUMENTS

| | | | |
|---|---|---|---|
| 2006/0067927 A1* | 3/2006 | Chandrasekaran | .... A61K 47/36 514/56 |
| 2014/0057311 A1 | 2/2014 | Kamm et al. | |
| 2014/0256831 A1 | 9/2014 | Ito et al. | |

(Continued)

FOREIGN PATENT DOCUMENTS

| | | |
|---|---|---|
| WO | 2018/026784 | 2/2018 |
| WO | 2020/210296 | 10/2020 |

OTHER PUBLICATIONS

Bartus et al (Experimental Neurology, vol. 235, Iss 1, May 2012, pp. 5-17). (Year: 2012).*

(Continued)

*Primary Examiner* — Benjamin J Packard
(74) *Attorney, Agent, or Firm* — Mueting Raasch Group

(57) ABSTRACT

Disclosed herein are compositions and methods for cellular reconstitution of photopolymerized, lyophilized, bioactive chondroitin sulfate glycosaminoglycan (CS-GAG)-based hydrogel matrices.

18 Claims, 29 Drawing Sheets

(56) References Cited

U.S. PATENT DOCUMENTS

| | | |
|---|---|---|
| 2015/0240194 A1 | 8/2015 | Neumann et al. |
| 2017/0022464 A1 | 1/2017 | Novak et al. |
| 2017/0211029 A1 | 7/2017 | Cha et al. |
| 2019/0017999 A1 | 1/2019 | Jeon et al. |
| 2020/0113837 A1 | 4/2020 | Karumbaiah et al. |
| 2022/0125731 A1 | 4/2022 | Karumbaiah et al. |

OTHER PUBLICATIONS

Yi et al, J Comp Neurol. Oct. 15, 2012; 520(15): 3295-3313. doi:10.1002/cne.23156 (Year: 2012).*

Shin et al., "Microfluidic assay for simultaneous culture of multiple cell types on surfaces or within hydrogels," 2012 Nature Protocols 7(7): 1247-1259.

Sugahara et al., "Chondroitin/dermatan sulfate in the central nervous system" 2007 Current Opinion in Structural Biology, 17: 536-545.

Sun et al., "Extracellular vesicles mediate neuroprotection and functional recovery after traumatic brain injury" Jun. 2020 Journal of Neurotrauma 37(11): 1358-1369.

Tondepu et al., "Glycomaterials to investigate the functional role of aberrant glycosylation in glioblastoma" Dec. 2021 Advanced Healthcare Materials e2101956.

Tysnes et al., "Stimulation of glioma-cell migration by laminin and inhibition by anti-alpha3 and anti-beta1 integrin antibodies" 1996 International Journal of Cancer 67: 777-784.

Valmikinathan et al., "Self assembled temperature responsive surfaces for generation of cell patches for bone tissue engineering" Sep. 2012 Biofabrication, 4: 035006.

Valmikinathan et al., "Photocrosslinkable chitosan based hydrogels for neural tissue engineering" Feb. 2012 Soft Matter 8(6): 1964-1976.

Zagzag, "Hypoxia-inducible factor 1 and VEGF upregulate CXCR4 in glioblastoma: Implications for angiogenesis and glioma cell invasion" 2006 Laboratory Investigation, 86: 1221-1232.

Zervantonakis et al., "Three-dimensional microfluidic model for tumor cell intravasation and endothelial barrier function" Aug. 2012 Procedures of the National Academy of Sciences, 109(34): 13515-13520.

Zhou et al., CXCR4 is a major chemokine receptor on glioma cells and mediates their survival Dec. 2002 The Journal of Biological Chemistry 277(51): 49481-49487.

Zhou et al., "Oversulfated chondroitin sulfate binds to chemokines and inhibits stromal cell-derived factor-1 mediated signaling in activated T cells" 2014 PLoS One, 9(4): e94402.

PCT/US2017/044845 filed Aug. 1, 2017; International Search Report and Written Opinion issued Oct. 6, 2017; 11 pages.

Karumbaiah et al., "Chondroitin sulfate glycosaminoglycan hydrogels create endogenous niches for neural stem cells" Oct. 2015 Bioconjugate Chemistry 26: 2336-2349.

Naderi-Meshkin et al., "Injectable hydrogel delivery plus preconditioning of mesenchymal stem cells: exploitation of SDF-1/CXCR4 axis toward enhancing the efficacy of stem cells' homing" 2016 Cell Biology International 40: 730-741.

PCT/US2017/044845 filed Aug. 1, 2017; International Preliminary Report on Patentability issued Feb. 14, 2019; 9 pages.

Andrews et al., "Chondroitin sulfate glycosaminoglycan scaffolds for cell and recombinant protein-based bone regeneration" 2019 Stem Cells Translational Medicine 8(6): 575-585.

Barbero et al., "Expression of the chemokine receptor CXCR4 and its ligand stromal cell-derived factor 1 in human prain tumors and their involvement in glial proliferation in vitro" Nov. 2002 Annals of the New York Academy of Sciences 973(1): 60-69.

Batzdorf et al., "The problem of multicentric gliomas" Feb. 1963 Journal of Neurosurgery, 20:122-136.

Berens et al., "The role of extracellular matrix in human astrocytoma migration and proliferation studied in a microliter scale assay" Clinical and Experimental Metastasis, 1994, 12: 405-415.

Betancur et al., "Chondroitin sulfate glycosaminoglycan matrices promote neural stem cell maintenance and neuroprotection post-traumatic brain injury" Mar. 2017 ACS Biomaterials Science and Engineering 3(3): 420-430.

Birdwhistell et al., "Sustained release of transforming growth factor-ß1 from platelet-rich chondroitin sulfate glycosaminoglycan gels" May 2018 Journal of Knee Surgery 31(5): 410-415.

Cai et al., "Semi-synthesis of chondroitin sulfate-E from chondroitin sulfate-A" Jan. 2012 Carbohydrate Polymers 37(1): 822-829.

Chagnon et al., "Functional significance of the LAR receptor protein tyrosine phosphatase family in development and diseases" Dec. 2004 Biochemistry and Cell Biology 82(6): 664-675.

Chopra et al., "Fully synthetic heparan sulfate-based neural tissue construct that maintains the undifferentiated state of neural stem cells" Sep. 2019 ACS Chemical Biology 14(9): 1921-1929.

Deepa et al., "Specific molecular interactions of oversulfated chondroitin sulfate E with various heparin-binding growth factors: Implications as a physiological binding partner in the brain and other tissues" Nov. 2002 The Journal of Biological Chemistry 277(46): 43707-43716.

Demuth and Berens, "Molecular mechanisms of glioma cell migration and invasion" 2004 Journal of Neuro-Oncology 70: 217-228.

Diaz et al., "Tks5-dependent, Nox-mediated generation of reactive oxygen species is necessary for invadopodia formation" Sep. 2009 Science Signaling 2(88): ra53.

Ehtesham et al., "CXCR4 expression mediates glioma cell invasiveness" Jan. 2006 Oncogene 25:2801-2806.

Funamoto et al., "A novel microfluidic platform for high-resolution imaging of a three-dimensional cell culture under a controlled hypoxic environment" Nov. 2012 Lab on a Chip 12(22): 4855-4863.

Giese et al., "Cost of migration: invasion of malignant gliomas and implications for treatment" Apr. 2003 Journal of Clinical Oncology 21(8):1624-1636.

Goffart et al., "Adult mouse subventricular zones stimulate glioblastoma stem cells specific invasion through CXCL12/ CXCR4 signaling" 2015 Neuro-Oncology 17(1): 81-94.

Hynes et al., "Contact and adhesive specificities in the associations, migrations, and targeting of cells and axons" Jan. 1992 Cell 68: 303-322.

Jeon et al., "Photocrosslinked alginate hydrogels with tunable biodegradation rates and mechanical properties" May 2009 Biomaterials 30: 2724-2734.

Karumbaiah et al., "Targeted downregulation of N-acetylgalactosamine 4-sulfate 6-O-sulfotransferase (GalNAc4S6ST) significantly mitigates chondroitin sulfate proteoglycan (CSPG) mediated inhibition" Jun. 2011 Glia 59(6): 981-996.

Karumbaiah et al., "Chondroitin sulfate glycosaminoglycans for CNS homeostasis-implications for material design" 2014 Current Medicinal Chemistry 21(37):4257-4281.

Kleihues et al., "World Health Organization classification of tumors" 2000 Cancer, 88: 2887.

Kobayashi et al., "Role of GalNAc4S-6ST in astrocytic tumor progression" 2013 PLoS One 8: e54278.

Laguri et al., "Relationships between glycosaminoglycan and receptor binding sites in chemokines—the CXCL12 example" 2008 Carbohydrate Research, 343: 2018-2023.

Latchoumane et al., "Chronic electrical stimulation promotes the excitability and plasticity of ESC-derived neurons following glutamate-induced inhibition in vitro," 2018 Scientific Reports 8: 10957.

Latchoumane et al., "Neurostimulation and reach-to-grasp function recovery following acquired brain injury: insight from pre-clinical rodent models and human applications" Jul. 2020 Frontiers in Neurology 11(835): 1-19.

Latchoumane et al., "Engineered glycomaterial implants orchestrate large-scale functional repair of brain tissue chronically after severe traumatic brain injury," Mar. 2021 Science Advances, 7: eabe0207.

Lau et al., "Pathophysiology of the brain extracellular matrix: a new target for remyelination" Oct. 2013 Nature Reviews Neuroscience, 14: 722-729.

Logun et al., "Glioma cell invasion is significantly enhanced in composite hydrogel matrices composed of chondroitin 4- and 4,6-sulfated glycosaminoglycans" 2016 Journal of Materials Chemistry B 4(36): 6052-6064.

(56) References Cited

OTHER PUBLICATIONS

Logun et al., "Microfluidics in malignant glioma research and precision medicine" May 2018 Advanced Biosystems 2 (5): 1700221.

Logun et al., "Surfen-mediated blockade of extratumoral chondroitin sulfate glycosaminoglycans inhibits glioblastoma Invasion," Nov. 2019 The Journal of the Federation of American Societies for Experimental Biology, 33(11): 11973-11992.

McCrary et al., "Cortical transplantation of brain-mimetic glycosaminoglycan scaffolds and neural progenitor cells promotes vascular regeneration and functional recovery after ischemic stroke in mice," Mar. 2020 Advanced Healthcare Materials, 9(5): e1900285.

Mackay, "Chemokines: immunology's high impact factors" 2001 Nature Immunology, 2: 95-101.

Mizumoto et al., "Interaction of chondroitin sulfate and dermatan sulfate from various biological sources with heparin-binding growth factors and cytokines" 2013 Glycoconjugate Journal 30: 619-632.

Mukhatyar et al., "Molecular sequelae of topographically guided peripheral nerve repair" Jul. 2014 Annals of Biomedical Engineering 42(7): 1436-1455.

Munson et al., "Anti-invasive adjuvant therapy with imipramine blue enhances chemotherapeutic efficacy against glioma" Mar. 2012 Science Translational Medicine 4(127): 127ra136.

Munson et al., "Interstitial flow in a 3D microenvironment increases glioma invasion by a CXCR4-dependent mechanism" Mar. 2013 Cancer Research 73(5): 1536-1546.

Nandini et al., "Novel 70-kDa chondroitin sulfate/dermatan sulfate hybrid chains with a unique heterogeneous sulfation pattern from shark skin, which exhibit neuritogenic activity and binding activities for growth factors and neurotrophic factors" Feb. 2005 The Journal of Biological Chemistry 280(6): 4058-4069.

Ostrom et al., "CBTRUS statistical report: Primary brain and central nervous system tumors diagnosed in the United States in 2008-2012" 2015 Neuro-Oncology 17: iv1-iv62.

Paganetti et al., "Glioblastoma infiltration into central nervous system tissue in vitro: involvement of a metalloprotease" Dec. 1988 The Journal of Cell Biology 107(6): 2281-2291.

Polacheck et al., "Tumor cell migration in complex microenvironments," Apr. 2013 Cellular and Molecular Life Sciences 70(8): 1335-1356.

Ramirez et al., "Glioblastoma multiforme therapy and mechanisms of resistance" Nov. 2013 Pharmaceuticals 6: 1475-1506.

Ruoslahti, "Brain extracellular matrix" 1996 Glycobiology, 6(5): 489-492.

Sanjay Sarma et al., "Lesion volume estimation from TBI-MRI" 2018 Progress in Advanced Computing and Intelligent Engineering, 563: 197-207.

Saxena et al., "Engineering controlled peritumoral inflammation to constrain brain tumor growth" Feb. 2019 Advanced Healthcare Materials 8(4): e1801076.

Schrappe et al., "Correlation of chondroitin sulfate proteoglycan expression on proliferating brain capillary endothelial cells with the malignant phenotype of astroglial cells" Sep. 1991 Cancer Research 51: 4986-4993.

Shen et al., "Extracellular matrix-based intracortical microelectrodes: Toward a microfabricated neural interface based on natural materials" 2015 Microsystems and Nanoengineering 1(1): 15010.

Kim et al., "A quantitative microfluidic angiogenesis screen for studying anti-anglogenic therapeutic Drugs", Lab Chip, 15, pp. 301-309 (2015).

Shin et al., "Microfluidic Study on ECM-dependent Three Dimensional Morphogenesis of Breast Adenocarcinoma Cells", 15th International Conference on Miniaturized Systems for Chemistry and Life Sciences Oct. 2-6, 2011, Seattle Washington, USA (2011).

Chung et al., "Cell migration into scaffolds under co-culture conditions in a microfluidic platform", Lab Chip, 9, pp. 269-276 (2009).

Kim et al., "Cooperative Roles of SDF-1 and EGF Gradients on Tumor Cell Migration Revealed by a Robust 3D Microfluidic Model", PLOS One, vol. 8, Issue 7, Jul. 2013, pp. 1-9.

Liu et al., "Development of a Biomimetic Chondroitin Sulfate-modified Hydrogel to Enhance to Metastasis of Tumor Cells", Scientific Reports, Jul. 19, 2016, pp. 1-13.

Nguyen et al., "Photopolymerizable hydrogels for tissue engineering applications", Biomaterials 23, 2002, pp. 4307-4314.

* cited by examiner

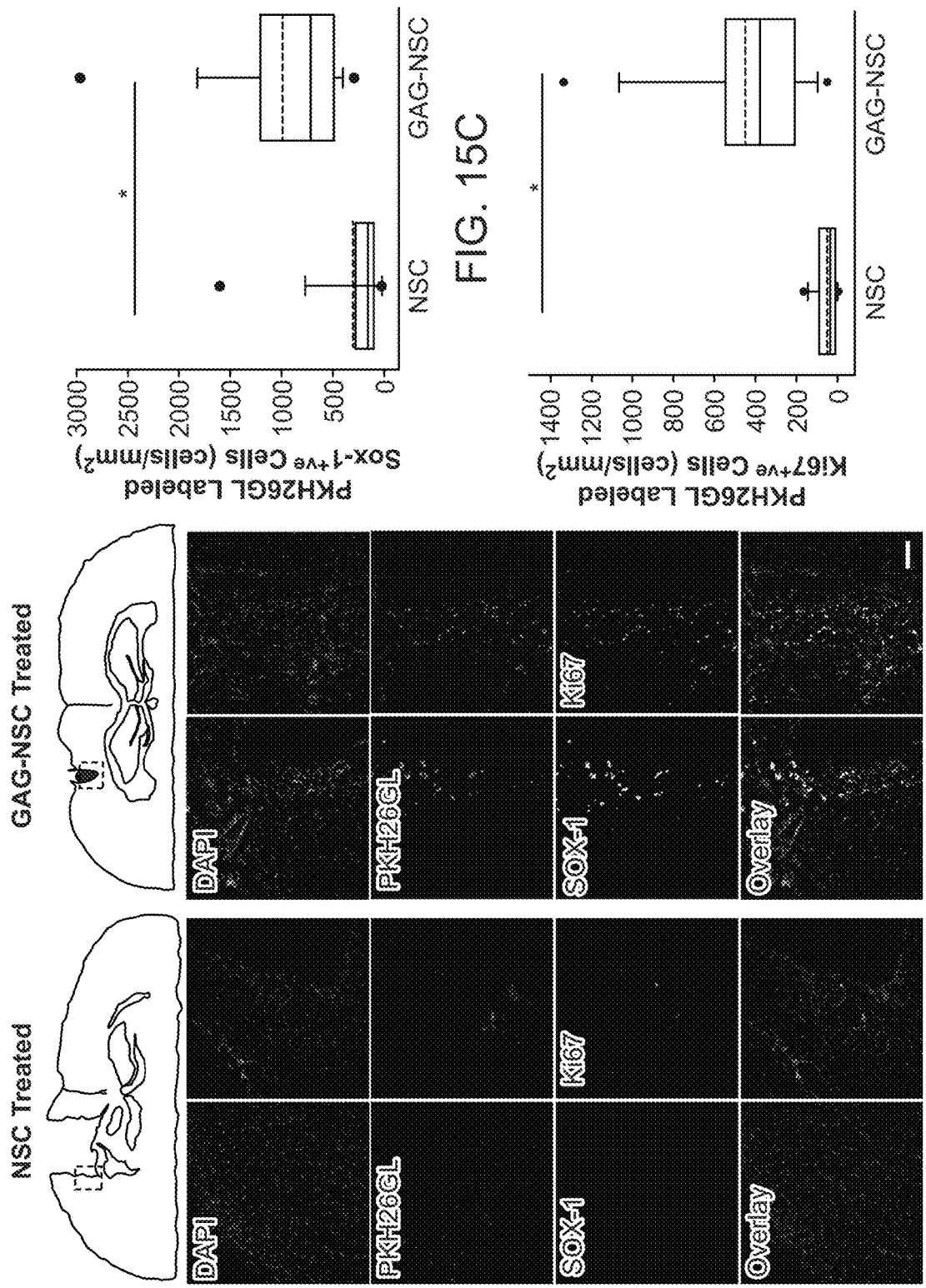

CHONDROITIN SULFATE GLYCOSAMINOGLYCAN HYDROGEL MATRICES FOR THE TREATMENT OF TRAUMATIC BRAIN INJURY

CONTINUING APPLICATION DATA

This application is a continuation application of U.S. patent application Ser. No. 16/322,680, filed Feb. 1, 2019, which is the § 371 U.S. National Stage of International Application No. PCT/US2017/044845, filed Aug. 1, 2017, which claims the benefit of U.S. Provisional Application No. 62/369,658, filed Aug. 1, 2016, the disclosures of which are incorporated by reference herein in their entireties.

GOVERNMENT FUNDING

This invention was made with government support under Grant No. R01 NS099596, awarded by the National Institutes of Health (NIH). The government has certain rights in the invention.

BACKGROUND

In vivo stem cell delivery after injury requires localized delivery and protection of transplanted cells within the defect. Hydrogels are the scaffolds of choice for these applications due to their utility as cell carriers and their tunable properties. However, current hydrogel based cell delivery methods are based on in situ thermal or chemical crosslinking methods to achieve cell encapsulation. These methods can negatively impact the viability and efficacy of transplanted cells due to carryover of, and exposure to unreacted chemicals, and exposure to adverse temperatures.

SUMMARY

Disclosed herein are compositions and methods for cellular reconstitution of photopolymerized, lyophilized, bioactive chondroitin sulfate glycosaminoglycan (CS-GAG)-based hydrogel matrices. Also disclosed are methods for direct injectable delivery of cell laden constructs using minimally invasive procedures.

As disclosed herein, purified and sterilized prefabricated photopolymerized CS-GAG hydrogels can be lyophilized, and subsequently rehydrated with the cell suspension. Moreover, the rehydrated stem cell laden CS-GAG hydrogels can subsequently be directly injected into a defect. This method of cellular encapsulation into hydrogel matrices can enhance cell viability, and can be applied to a host of other cell transplantation and trophic factor delivery applications.

Therefore, disclosed herein is a method for encapsulating cells, comprising providing a composition comprising a lyophilized chondroitin sulfate glycosaminoglycan (CS-GAG) hydrogel, and rehydrating the lyophilized CS-GAG hydrogel with a composition comprising cells suspended in an aqueous medium, thereby encapsulating the cells in CS-GAG hydrogel.

In some embodiments, the cells comprise stem cells. For example, the cells can be neural stem cells. Therefore, the composition comprising the cells and/or the lyophilized CS-GAG hydrogel further comprises one or more trophic factors, such as FGF-2, BDNF, EGF, and/or IL10. In one aspect, the composition comprising the cells and/or the lyophilized CS-GAG hydrogel can further comprise adhesion molecules and/or adhesion molecule receptors, such as, CXCR4, CXCR7, and/or FAK.

Also disclosed herein are methods of treating TBI in a subject comprising administering to the subject at the site of a TBI a CS-GAG hydrogel comprising a neural cell (such as, for example, a neural stem cell), one or more trophic factors (such as, for example, FGF-2, BDNF, EGF, and/or IL10), and/or one or more adhesion molecules and/or adhesion molecule receptors (such as, for example, CXCR4, CXCR7, and/or FAK).

In some embodiments, the lyophilized CS-GAG hydrogel is sterilized prior to rehydration using gamma irradiation or ethylene oxide.

In some embodiments, the disclosed method further comprises transplanting the encapsulated cells into a subject.

In some embodiments, the trophic factors, adhesion molecules, and/or adhesion molecule receptors are YYY Also disclosed is a kit for encapsulating cells, comprising a lyophilized chondroitin sulfate glycosaminoglycan (CS-GAG) hydrogel and a rehydration solution suitable for cell suspension. In some embodiments the kit further comprises one or more trophic factors. For example, the trophic can be present in the rehydration solution and/or the lyophilized hydrogel.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows 500× and 1000× (insert) magnification images of 0.5% AG, 0.5% HA, and 2% CS-A hydrogels showing relative porosity. Scale bars=100 μm. FIG. 1B shows pore size measurements done through quantitative ImageJ analysis shows comparable pore sizes in each hydrogel model. FIG. 1C shows storage modulus measured using a parallel-plate rheometer over a standard 0-100 rad/sec frequency sweep for all hydrogels.

FIG. 3A shows a schematic of three-channeled PDMS microfluidic devices. Channels are 1000 μm in width, with 100 μm trapezoidal barriers between channels and 4 mm diameter wells. Cells were seeded into center channels, with hydrogel choices placed into right and left channels. Representative 40× oil images of GFP/Hoechst-stained cells from each hydrogel channel shown below. Scale bar=100 μm. Quantification of cell migration into from each type of choice assay was performed across n=4 for each choice. All choice assays were performed against the monosulfated CS-A. Significance and differences were represented by '*' indicating p<0.05. No significance is represented by 'ns. ' FIG. 3B shows a 10× tiled image showing cell invasion into hydrogel choices. Areas represented by ROIs (red and yellow) indicate hydrogel channel and exclude cell-containing center channel. Scale bar=1000 μm. FIG. 3C shows that blue ROI represents trapezoidal barriers, with 10× representative images of cells infiltrating into CS-A hydrogels at 6 h post cellseeding. Scale bar=100 µm.

FIG. 4A shows FAK (yellow) and vinculin (red) demonstrates evidence of cell migration in hydrogel matrices; FIG. 4B shows quantification of % F-actin containing cells. Scale bar=100 µm. FIG. 4C shows phalloidin staining (red) to visualize Factin polymerization among cells in each choice assay. FIG. 4D shows t-test quantifications (p<0.05). Cells were also Hoechst stained (blue) to show cell nuclei. Scale bar 100 µm. Means with '*' (p<0.05) are significantly different, 'ns' represents no significant difference.

FIG. 5A shows proof of establishment of a chemokine gradient performed using Alexa Fluor 488-conjugated bovine aprotinin. Fluorescence was quantified at zero, three and six hour time points (six hour time point data shown in graph compared to zero hours). No significant differences in chemokine gradient diffusion was detected across different hydrogels as evaluated using a one-way ANOVA. Representative images shown from each time point to demonstrate chemokine diffusion through hydrogel matrices after 6 hours. Scale bar 100 µm. Representative 40×GFP/Hoechst images of migrating cells in response to CXCL12 presence in hydrogel matrices after 6 hours. Scale bar=100 µm.

FIG. 7A shows a schematic demonstrating ELISA methods to determine amount of bound CXCL12 to biotinylated HA, CS-A and COMP GAGs. FIG. 7B shows data representing mean OD values obtained across four different CXCL12 concentrations against each GAG analyzed in quadruplicate. Data are represented as mean+SD, and means with '*' (p<0.05) are significantly different from other treatments.

FIGS. 9A, 9B, and 9C shows strong Anion Exchange (SAX) HPLC of: (FIG. 9A) CS-standards (FIG. 9B) monosulfated CSA (D0a4), consisting of trace amounts of monosulfated CS-C (D0a0) and (FIG. 9C) Regioselective sulfation of CS-A yielding dual sulfated semisynthetic CS-E (Doa10, 52%), which along with minor increases in 20 sulfation also consists of 17% CS-C and 19% CS-A.

FIG. 10A shows the three main channels are 1000 µm wide with wells at each end measuring 5 mm in diameter. Insert shows (FIG. 10B) trapezoidal barriers that line the inner channel, with dimensions chosen to allow for the selective cell migration between channels without allowing hydrogel contents to mix within the middle channel.

FIG. 12A shows bright-field image of the interface (indicated by white dotted line) of the CS-GAG and HA matrices. FIG. 12B shows Wisteria floribunda (WFA) agglutinin labeling (pseudocolored yellow) of CS-GAG matrix. FIG. 12C shows the area of FGF2 binding and retention (pseudocolored red); FIG. 12D shows the overlay of WFA and FGF2 labeling demonstrating the preferential FGF2 binding and retention in the CS-GAG matrix when compared to surrounding HA matrix. Scale=100 µm.

FIG. 13A shows representative images of the region corresponding to the red dotted region of interest (ROI) surrounding a portion of the SVZ in coronal brain sections. A tiled representation of the lateral ventricle is presented on the left of figure panel; Scale=300=m. Cellular nuclei are represented by DAPI (blue); CS-GAG and GalNAc presence in the corpus callosum and in the SVZ is indicated by WFA labeling (green); FGF-2 labeling is indicated in magenta; Proliferating Ki67+ cells are represented in grayscale; Merged overlays are presented in the bottom most panel; Scale=100=m. Significantly greater colocalization of FGF-2 and WFA was observed in the SVZ when compared to the cortex (FIG. 13B); and there was a high correlation of Ki67+ cells and WFA % colocalization with FGF-2 and WFA % colocalization (FIG. 13C). Statistical significance is represented by '*' which indicates p<0.05.

(FIG. 14B) NSC only; (FIG. 14C) CS-GAG only; and (FIG. 14D) CSGAG-NSC treatments. (FIG. 14E) Brain sections from CS-GAG only and CSGAG-NSC treatments demonstrate significantly enhanced neuronal presence when compared to TBI control and NSC only treatments. Statistical significance is represented by '*', which indicates p<0.05. The lack of statistical significance between groups is denoted by 'n.s'. Scale=1 mm.

FIGS. 15A, 15B, 15C, and 15D show that transplanted NSCs survive and proliferate 4 weeks post-TBI. Representative images of the region corresponding to the red dotted box surrounding the lesion area in coronal brain sections obtained from (FIG. 15A) NSC only, and (FIG. 15B) CS-GAG-NSC treated animals. Cellular nuclei are represented by DAPI (blue); transplanted NSCs are represented by PKH26GL labeled cells (red); undifferentiated NSC are represented by Sox1 labeling (yellow); proliferating NSCs are represented by Ki67 labeling (green). Merged overlays are presented in the bottom most panel. Significantly greater PKH26GL+ Sox1+ (FIG. 15C), and Ki67+ (FIG. 15D) NSCs were visualized in CS-GAG-NSC treated animals when compared to NSC only treated animals. Statistical significance is represented by '*', which indicates p<0.05. Scale=100 μm.

FIG. 16A shows representative images of the region corresponding to the red dotted box in coronal brain sections obtained from sham animals, and surrounding the lesion area in coronal brain sections obtained from TBI only, NSC only, CS-GAG only, and CSGAG-NSC treated animals. Cellular nuclei are represented by DAPI (blue); CS-GAG and GalNAc presence is indicated by WFA labeling (green); and FGF2 labeling is indicated in magenta. Merged overlays are presented in the topmost panel. FIG. 16B shows that a significantly greater FGF2+ area was visualized in brain sections obtained from CS-GAG and CS-GAG-NSC treated animals when compared to sham and TBI only controls, and NSC only treated animals. Statistical significance is represented by '*', which indicates p<0.05. Scale=100 μm.

FIG. 17B represents the neural cell differentiation of transplanted NSCs. Cellular nuclei are represented by DAPI (blue); transplanted NSCs are represented by PKH26GL labeled cells (red); NSCs differentiating into neurons are represented by NeuN labeling (green); NSC differentiating into oligodendrocytes are represented by the Olig2 label (yellow); undifferentiated NSCs are represented by the Sox1 label (magenta); Merged overlays are presented in the bottom most panels. Scale=100 μm. FIG. 17C shows that a significantly greater number of NSCs delivered in CS-GAG matrices maintained their undifferentiated state as demonstrated by the maintenance of Sox1 expression when compared to NSCs that differentiated into neurons or oligodendrocytes. Statistical significance is represented by '*', which indicates p<0.05. FIG. 17D shows high-magnification images of PKH26GL+ transplanted NSCs in the lesion site coexpressing the NSC markers Sox1 and nestin. Scale=20 μm.

FIG. 18A shows representative images of the region corresponding to the red dotted box surrounding the lesion area in coronal brain sections obtained from TBI only control, and CS-GAG-NSC treated animals. Cellular nuclei are represented by DAPI (blue); activated macrophages are represented by CD68 labeled cells (green); and reactive astrocytes are represented by GFAP labeled cells (red). Merged overlays are presented in the bottom right panels in each group. FIG. 18B shows that significantly greater CD68+ reactivity was observed in brain sections obtained from animals treated with NSCs only, and with CS-GAG-NSCs when compared to all other groups. FIG. 18C shows brain tissue obtained from TBI only controls indicated a significantly increased GFAP immunoreactivity for reactive astrocytes when compared to all treatment groups and sham control. Statistical significance is represented by '*' which indicates p<0.05. The lack of statistical significance between groups is denoted by 'n.s'. Scale=100 μm.

DETAILED DESCRIPTION

Figure 1A:
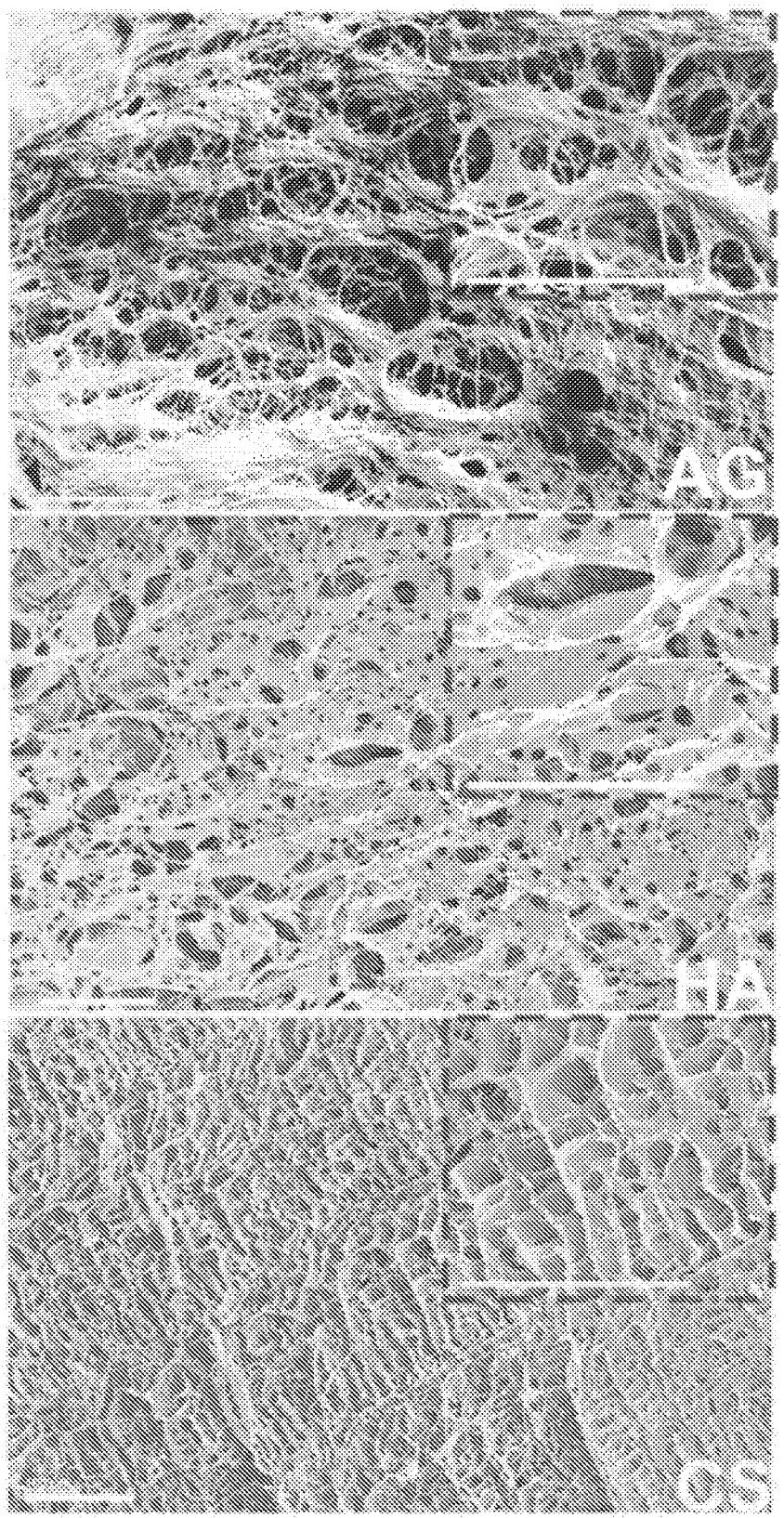
FIGS. 1A, 1B, and 1C show evaluation of the biomechanical properties of hydrogel matrices.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

Disclosed herein are compositions and methods for cellular reconstitution of photopolymerized, lyophilized, bioactive chondroitin sulfate glycosaminoglycan (CS-GAG)-based hydrogel matrices. It is understood and herein contemplated that chondroitin sulfate glycosaminoglycan (CS-GAG)-based hydrogel matrices can provide a matrix for encapsulating cells. This same matrix can be applied to treat traumatic brain injury (TBI). Accordingly, in one aspect, disclosed herein are CS-GAG hydrogels.

The disclosed CS-GAG hydrogels can comprise additional factors that stimulate cell proliferation and growth. For example, the CS-GAG hydrogels can be sulfonated (for example monosulfonated or disulfonated), comprise one or more adhesion molecules and/or adhesion molecule receptors, and/or one or more trophic factors. Accordingly, in one aspect, disclosed herein are CS-GAG hydrogels wherein the hydrogel is sulfonated. Also disclosed herein are CS-GAG hydrogels (sulfonated or non-sulfonated) that further comprise one or more adhesion molecules and/or adhesion molecule receptors, and/or one or more trophic factors.

As used herein "adhesion molecules and/or adhesion molecule receptors" can include receptors such as chemokine receptors (such as, for example CXCR4 and/or CXCR7) and adhesion molecules such as, for example, focal adhesion kinase (FAK). Other such adhesion molecules and/or adhesion molecule receptors can include but are not limited to integrins (such as, for example, CD49a, CD49b, CD11a, CD11, CD29, CD18, CD61, and CD103), Immunoglobulin superfamily cell adhesion molecules (Intercellular cell adhesion molecule (ICAM-1), vascular cellular adhesion molecule (VCAM-1), and neural cell adhesion molecules (NCAM)), cadherins (such as, for example, epithelial cadherein (E-cadherein), neural cadherein (N-cadherein), N-cadherein 2, and placental cadherein (P-cadherein), and selectins (such as, for example, E-selectin, L-selectin, and P-selecting). For example, disclosed herein are CS-GAG hydrogels comprising CXCR4, CXCR7, and/or FAK.

As used herein, "trophic factors" refers to growth factors that stimulate the growth of cells maintained in the CS-GAG hydrogel. For example, "trophic factors" can comprise Epidermal Growth Factor (EGF); CXCL12; Fibroblast Growth Factors (FGF) such as, for example, FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22, and FGF23; Erythropoietin (EPO); granulocyte macrophage colony-stimulating factor (GM-CSF); interleukin-6 (IL-6); angiopoietin; interleukin-2 (IL-2); interleukin-4 (IL-4); interleukin-3 (IL-3); interleukin-5 (IL-5); interleukin-7 (IL-7); interleukin-10 (IL-10); neurotrophin-3; neurotrophin-4; nerve growth factor (NGF); brain-derived neurotrophic factor (BDNF); platelet derived growth factor (PDGF); placental growth factor; macrophage stimulating protein; neuregulins (such as, for example NRG1, NRG2, NRG3, and NRG4); vascular endothelial growth factor (VEGF); tumor necrosis factor alpha (TNF-α); and transforming growth factors TGF-α and TGF-β. For example, disclosed herein are CS-GAG hydrogels comprising FGF2, IL-10, BDNF, CXCL12, and/or EGF.

The disclosed CS-GAG hydrogels can also be purified and sterilized and prefabricated for commercial use. The CS-GAG hydrogels can also be lyophilized, and subsequently rehydrated with the cell suspension.

The disclosed hydrogels can be used to encapsulate cells. The term "cell" refers to individual cells, cell lines, primary culture, or cultures derived from such cells unless specifically indicated. These different cell types include, but are not limited to, Keratinizing Epithelial Cells, Wet Stratified Barrier Epithelial Cells, Exocrine Secretory Epithelial Cells, Hormone Secreting Cells, Epithelial Absorptive Cells (Gut, Exocrine Glands and Urogenital Tract), Metabolism and Storage cells, Barrier Function Cells (Lung, Gut, Exocrine Glands and Urogenital Tract), Epithelial Cells Lining Closed Internal Body Cavities, Ciliated Cells with Propulsive Function, Extracellular Matrix Secretion Cells, Contractile Cells, Blood and Immune System Cells, Sensory Transducer Cells, Autonomic Neuron Cells, Sense Organ and Peripheral Neuron Supporting Cells, Central Nervous System Neurons and Glial Cells, Lens Cells, Pigment Cells, Germ Cells, and Nurse Cells. Also included are any stem cells and progenitor cells of the cells disclosed herein, as well as the cells they lead to. Cells and cell types of interest produced in the disclosed method can be identified by reference to one or more characteristics of such cells.

The term "stem cell" refers to cells that are capable of extensive proliferation, creating more stem cells (self-renewal) as well as more differentiated cellular progeny (multipotent or pluripotent). In mammals, there are two broad types of stem cells: embryonic stem cells, which are isolated from the inner cell mass of blastocysts, and adult stem cells, which are found in various tissues. Examples of adult stem cells include hematopoietic stem cells, mammary stem cells, intestinal stem cells, mesenchymal stem cells (MSCs), endothelial stem cells, neural stem cells (NSCs), olfactory adult stem cells, neural crest stem cells, and testicular stem cells.

The disclosed CS-GAG hydrogels can be produced and polymerized using standard methods, such as those described in Karumbaiah, L. et al., Bioconjug Chem, 2015, 26:2336-2349, which is incorporated by reference herein in its entirety for the teachings of CS-GAG hydrogels. For example, the disclosed CS-GAG hydrogels can be composed of monosulfated CS-4 (CS-A), CS-6 (CS-C), and/or disulfated CS-4,6 (CS-E). In addition, methacrylate groups can be incorporated onto CS-GAG polymer by the addition of 2-aminoethyl methacrylate (AEMA) to the carboxylic acid groups on the glucuronic acid residues using carbodiimide chemistry. The polymerization can occur by any means known in the art including, but not limited to photopolymerization. Accordingly, in one aspect, disclosed herein are CS-GAG hydrogels wherein the hydrogel is photopolymerized.

It is understood and herein contemplated that the disclosed CS-GAG hydrogels can be used to encapsulate cells. Thus, in one aspect disclosed herein are methods for encapsulating cells, comprising providing a composition comprising a lyophilized chondroitin sulfate glycosaminoglycan (CS-GAG) hydrogel, and rehydrating the lyophilized CS-GAG hydrogel with a composition comprising cells suspended in an aqueous medium, thereby encapsulating the cells in CS-GAG hydrogel.

Also disclosed herein are methods of encapsulating cells, wherein the CSC-GAG hydrogel is photopolymerized.

The disclosed encapsulating methods can provide for direct injectable delivery of cell laden constructs using minimally invasive procedures. As disclosed herein, purified and sterilized (including sterilization by gamma irradiation or ethylene oxide) prefabricated photopolymerized CS-GAG hydrogels can be lyophilized, and subsequently rehydrated with the cell suspension. Moreover, the rehydrated stem cell laden CS-GAG hydrogels can subsequently be directly injected into a defect. This method of cellular encapsulation into hydrogel matrices can enhance cell viability, and can be applied to a host of other cell transplantation and trophic factor delivery applications.

Therefore, disclosed herein is a method for encapsulating cells, comprising providing a composition comprising a lyophilized chondroitin sulfate glycosaminoglycan (CS-GAG) hydrogel, and rehydrating the lyophilized CS-GAG hydrogel with a composition comprising cells suspended in an aqueous medium, thereby encapsulating the cells in CS-GAG hydrogel. In one aspect, the disclosed methods can further comprise transplanting the encapsulated CS-GAG hydrogel (comprising cells, trophic factors, and/or adhesion molecules and/or adhesion molecule receptors) into a subject.

In some embodiments, the lyophilized CS-GAG hydrogel is photopolymerized. Thus disclosed herein are methods for encapsulating cells, wherein the CS-GAG hydrogel is photopolymerized.

As noted above, in some embodiments, the cells comprise stem cells. For example, the cells can be neural stem cells. Therefore, the composition comprising the cells and/or the lyophilized CS-GAG hydrogel further can further comprises one or more trophic factors, such as FGF-2, BDNF, EGF, and/or IL10. Accordingly, in one aspect, disclosed herein are methods for encapsulating cells, comprising providing a composition comprising a lyophilized chondroitin sulfate glycosaminoglycan (CS-GAG) hydrogel, wherein the CS-GAG hydrogel further comprises one or more trophic factors, such as FGF-2, BDNF, EGF, and/or IL10.

The disclosed methods can further comprise adhesion molecules and/or adhesion molecule receptors to stimulate proliferation of cells encapsulated by or adjacent to the hydrogel. Therefore, the composition comprising the cells and/or the lyophilized CS-GAG hydrogel further can further comprises one or more adhesion molecules and/or adhesion molecule receptors, such as, CXCR4, CXCR7, and/or FAK. Accordingly, in one aspect, disclosed herein are methods for encapsulating cells, comprising providing a composition comprising a lyophilized chondroitin sulfate glycosaminoglycan (CS-GAG) hydrogel, wherein the CS-GAG hydrogel further comprises one or more adhesion molecules and/or adhesion molecule receptors, such as, CXCR4, CXCR7, and/or FAK.

As noted above, the method of cellular encapsulation into hydrogel matrices can enhance cell viability, and can be applied to a host of other cell transplantation and trophic factor delivery applications. For example, the CS-GAG hydrogels disclosed herein can be directly injected into a void created from traumatic brain injury (TBI) to stimulate regeneration of injured brain tissue. Thus, in one aspect, disclosed herein are methods of treating TBI in a subject comprising administering to the subject at the site of a TBI a CS-GAG hydrogel comprising a neural cell (such as, for example, a neural stem cell), one or more trophic factors (such as, for example, FGF-2, BDNF, EGF, and/or IL10), and/or one or more adhesion molecules and/or adhesion molecule receptors (such as, for example, CXCR4, CXCR7, and/or FAK).

In one aspect, the CS-GAG used in the methods of treating TBI can be a sterilized and lyophilized CS-GAG which would be rehydrated at time of administration. Accordingly, disclosed herein are methods of treating TBI, wherein the CS-GAG is lyophilized and the method further comprises rehydrating the lyophilized CS-GAG hydrogel with a rehydration solution composition comprising cells suspended in an aqueous medium. In one aspect, also disclosed are methods of treating TBI, wherein the one or more trophic factors, adhesion molecules, or adhesion molecule receptors are present in the rehydration solution.

It is understood and herein contemplated that the disclosed CS-GAG hydrogels can be packaged as a kit to enable the practice of the methods of encapsulating cells and treating TBI disclosed herein. Accordingly, disclosed herein are kits for encapsulating cells and/or treating TBI comprising a composition comprising a lyophilized chondroitin sulfate glycosaminoglycan (CS-GAG) hydrogel and a rehydration solution suitable for cell suspension.

The disclosed kits can further comprise one or more trophic factors (such as, for example, FGF-2, BDNF, EGF, and/or IL10), and/or one or more adhesion molecules and/or adhesion molecule receptors (such as, for example, CXCR4, CXCR7, and/or FAK). In one aspect, the trophic factors and/or adhesion molecules and/or adhesion molecule receptors can be present in the rehydration solution.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Glioma Cell Invasion is Significantly Enhanced in Composite Hydrogel Matrices Composed of Chondroitin 4- and 4,6-Sulfated Glycosaminoglycans Glioblastoma multiforme (GBM) is the most aggressive form of astrocytoma that accounts for the majority of primary malignant brain tumors among adults in the United States (Ostrom, Q. T. et al., Neuro-oncology, 2015, 17 Suppl 4, iv1-iv62). The spread of GBM involves the diffuse invasion of single glioma cells along blood vessels and white matter tracts in brain tissue (Esiri, M. Journal of neurology, neurosurgery, and psychiatry, 2000, 68:538D). The tumorous growth penetrates through key functional regions of the brain, and culminates with the formation of a large GBM mass surrounded by invasion along white matter tracts into nearby brain structures. Eventually, these brain tumors outgrow the limited space available in the brain and disturb other precious structures, rendering cognitive and motor processes damaged. Complete surgical resection is often the first course of action, but current therapies are ineffective in destroying migrating cells after they have left the de novo tumor mass (Giese, A. et al., J Clin Oncol, 2003, 21:1624-1636; Ramirez, Y. P. et al., Pharmaceuticals (Basel), 2013, 6:1475-1506; Batzdorf, U. et al., Journal of neurosurgery, 1963, 20:122-136).

The mechanism of glioma invasion is unknown. Primary glial cell tumors and early glial precursors possess the ability to invade through brain tissue, which is otherwise resistant to tumor invasion (Paganetti, P. A. et al., J Cell Biol, 1988, 107:2281-2291). Primary glial tumors also rarely metastasize outside the brain (Kleihues, P. et al., Cancer, 2000, 88:2887). This evidence points to a specialized glial cell interaction with the brain tissue extracellular matrix (ECM) that can directly induce glioma cell invasion. Cellular migration includes adhesion factor expression, cytoskeletal rearrangement, and secretion of ECM-remodeling enzymes (Demuth, T. et al., Journal of neuro-oncology, 2004, 70:217-228). Recent evidence suggests that cell-ECM interactions trigger the formation of invadopodia and cytoskeletal modifications, both of which are indicators of invasion (Diaz, B. et al., Sci Signal, 2009, 2:ra53; Munson, J. M. et al., Sci Transl Med, 2012, 4:127ra136).

Brain extracellular matrix (ECM) molecules play an important role in regulating cell migration throughout development, and aberrant ECM conditions can directly promote cancer cell migration (Berens, M. E. et al., Clinical & experimental metastasis, 1994, 12:405-415; Hynes, R. O. et al., Cell, 1992, 68:303-322; Tysnes, B. B. et al., Journal international du cancer, 1996, 67:777-784). Healthy brain parenchyma is composed mostly of CSPGs and hyaluronic acid (HA), along with a smaller component of fibrillar proteins such as laminins, collagens, and fibronectin (Lau, L. W. et al., Nature reviews. Neuroscience, 2013, 14:722-729). CS-GAGs side-chains consisting of N-acetyl-D-galactosamine and D-glucaronic acid repeating disaccharide units are directly linked to the CSPG core protein. CS-GAGs linked to CSPGs are known to bind and organize brain ECM, regulate neuronal outgrowth, and provide trophic factor retention (Ruoslahti, E. Glycobiology, 1996, 6:489-492). The majority of CS-GAGs in the brain are monosulfated (CS-A) with smaller percentages of chondroitin-6-sulfate (CS-C) and CS-E (Sugahara, K. et al., Current opinion in structural biology, 2007, 17:536-545). However, this composition is dramatically altered immediately around invasive brain tumors, which have been reported to upregulate CSPGs and enzymes that affect sulfation patterns of CS-GAGs (Kobayashi, T. et al., PLoS One, 2013, 8:e54278; Schrappe, M. et al., Cancer research, 1991, 51:4986-4993). Although the upregulation of CSPGs around invasive brain tumors has long been reported, the precise role of sulfated CS-GAGs in promoting glioma invasion has not yet been elucidated. An abundance of oversulfated CS-GAGs in the brain tumor microenvironment combined with their ability to bind cell-motility and adhesion molecules (Deepa, S. S. et al., The Journal of biological chemistry, 2002, 277:43707-43716; Mizumoto, S. et al., Glycoconjugate journal, 2013, 30:619-632; Nandini, C. D. et al., The Journal of biological chemistry, 2005, 280:4058-4069; Zhou, Z. H. et al., PLoS One, 2014, 9:e94402), is suggestive of a potential CS-GAG sulfation-driven mechanism that contributes to brain tumor invasion.

Primary brain tumors spread towards new areas with desirable environmental conditions for growth, and this navigation is guided by tissue composition and extracellular haptotactic signals (Mackay, C. R. Nature immunology, 2001, 2:95-101). The chemokine CXCL12 (stromal-derived factor-1alpha (SDF-1α) has been previously reported to bind to the cell-surface receptor CXCR4 to induce the growth of glioma cells (Barbero, S. et al., Ann N Y Acad Sci, 2002, 973:60-69; Goffart, N. et al., Neuro-oncology, 2015, 17:81-94). CXCL12 is found along white matter tracts and blood vessels in the brain, providing glioma cells with a haptotactic roadmap to invade through the brain interstitial matrix (Zagzag, D. et al., Laboratory investigation; a journal of technical methods and pathology, 2006, 86:1221-1232). The CXCR4 receptor has been documented as being highly expressed in GBMs and identified as a regulatory element in glioma invasion, with the brain microenvironment potentially playing a role in glioma cell interaction with CXCL12 (Ehtesham, M. et al., Oncogene, 2006, 25:2801-2806; Laguri, C. et al., Carbohydrate research, 2008, 343:2018-2023; Munson, J. M. et al., Cancer research, 2013, 73:1536-1546; Zhou, Y. et al., The Journal of biological chemistry, 2002, 277:49481-49487). Since sulfated CS-GAGs interact with ECM proteins and influence cellular processes, the formation of a complex between sulfated CS-GAGs and the CXCL12 protein has the potential to initiate or mediate glioma cell invasion.

Cancer cells are also known to bind CSPGs through the leukocyte common antigen-related (LAR) subfamily of receptor protein tyrosine phosphatases, known for their role in regulating cellular proliferation and adhesion (Chagnon, M. J. et al., Biochemistry and cell biology Biochimie et biologie cellulaire, 2004, 82:664-675). LAR receptors have been implicated in malignant breast cancers and can potentially bolster the interaction of glioma cells with the CS-GAG rich brain ECM to promote invasion. Unregulated activity from overexpression of LAR receptors could contribute to neoplastic generation or stimulate diffuse single cell migration deeper into the brain via independent signaling mechanisms.

In this study a microfluidics-based in vitro assay platform was used to elucidate the specific relationship between CS-GAG sulfation and glioma cell invasion. A rigorous physical and mechanical characterization of sulfated CS-GAG, unsulfated HA, and unsulfated AG hydrogel matrices was conducted to ensure uniformity of their biophysical and biomechanical properties. Cell migration and haptotaxis of human glioma cells encapsulated within different hydrogel matrices were quantified to determine the influence of the extracellular microenvironment on cell invasion. Enzyme linked immunosorbent assays (ELISAs) were used to evaluate specific binding affinities of CXCL12 to immobilized unsulfated, monosulfated, and disulfated GAGs. Finally the expression levels of CXCL12, CXCR4, and the CSPG-binding LAR-receptor protein tyrosine phosphatase (RPTP) transcripts in cells encapsulated in different hydrogels were investigated using qRT-PCR assays and western blotting.

Experimental Procedures

Synthesis of Methacrylated Monosulfated Chondroitin Sulfate (mCS-A), Disulfated Methacrylated Chondroitin Sulfate (mCS-E) and Hyaluronic Acid (mHA)

CS-A hydrogels were fabricated using a mixture of chondroitin sulfate A/C powder (86% A/5% C/6% E) derived from bovine trachea (Sigma Aldrich, MO), and using methods as described previously (Karumbaiah, L. et al., Bioconjug Chem, 2015, 26:2336-2349; Jeon, O. et al., Biomaterials, 2009, 30:2724-2734). Briefly, 500 mg of chondroitin sulfate was dissolved in 50 mM 2-morpholinoethanesulfonic acid (MES; Sigma Aldrich) buffer (pH 6.5) with 0.5 M NaCl. 45.6 mM EDC (Thermo, IL) was added to activate carboxylic groups on glucuronic acid residues of CS, along with 22.8 mM NHS (Thermo, IL) to control carbodiimide crosslinking between the carboxyl groups on CS and the amine group of AEMA. 22.8 mM AEMA (Polysciences Inc., PA) was added and the reaction was allowed to proceed for 24 h. The next day, the product was precipitated by adding 1:1 ratio of acetone and rotary evaporated to dryness. The dried mCS was dissolved in deionized water to the original volume and dialyzed for 3 days using 1000 MWCO dialysis tubing (Spectrum Laboratories Inc., CA). The dialyzed product was lyophilized and stored in desiccant at −20° C. until used. The resulting mCS-A was used to make 2% w/v CS-A hydrogel with 0.05% 2-hydroxy-4'-(2-hydroxyethoxy)-2-methylpropiophenone (Irgacure-2959, Sigma Aldrich) in DMEM/F-12 (Corning, NY), then crosslinked upon exposure to 365 nm UV light (160 BlakRay UVP, CA).

Figure 9A:
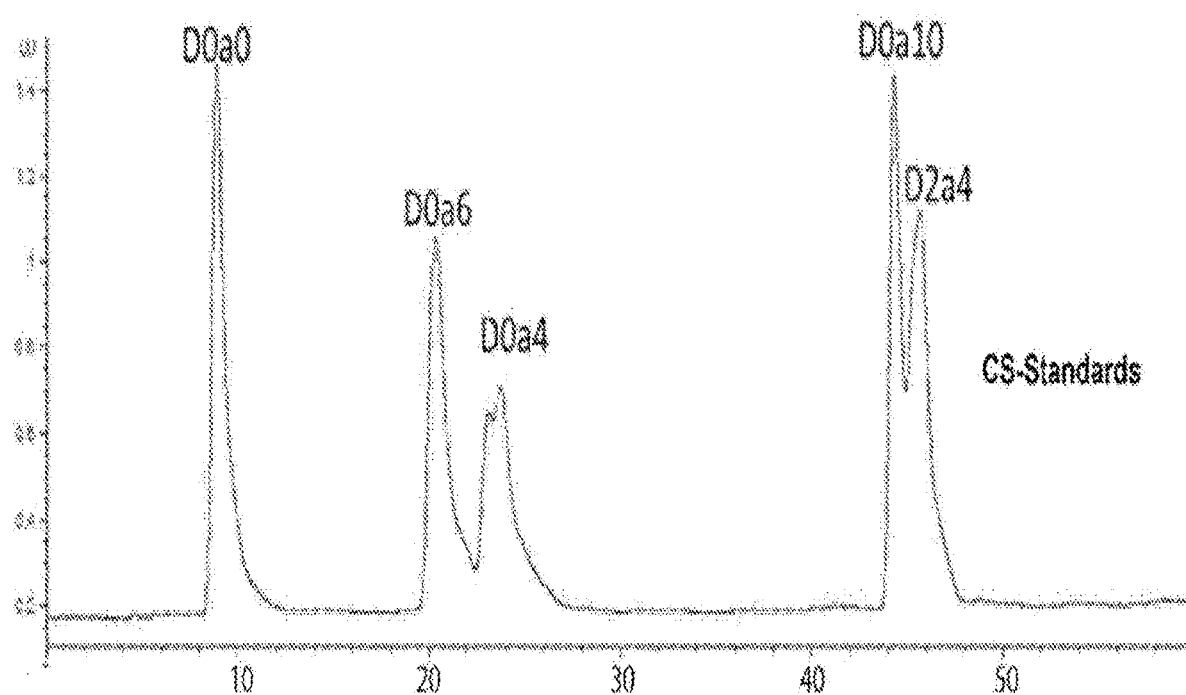
Figure 9B:
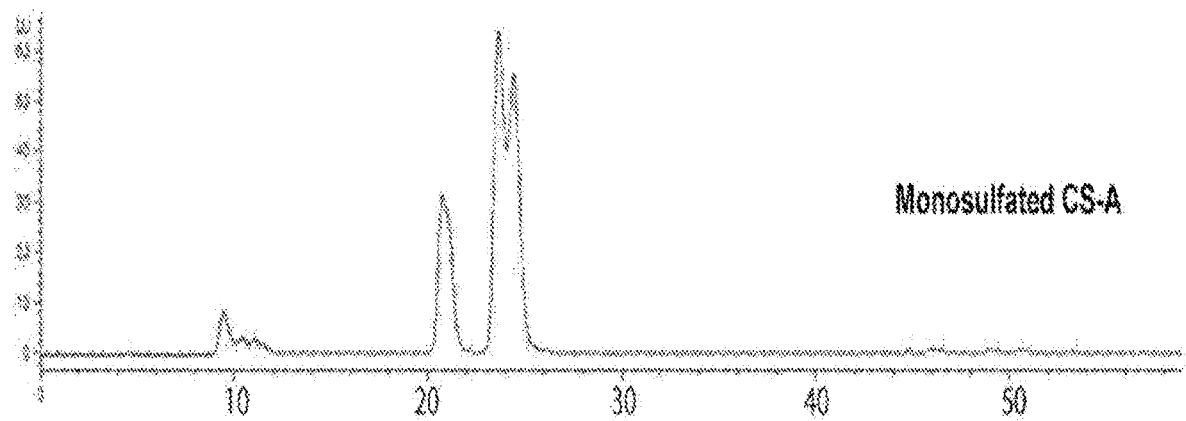
Figure 9C:
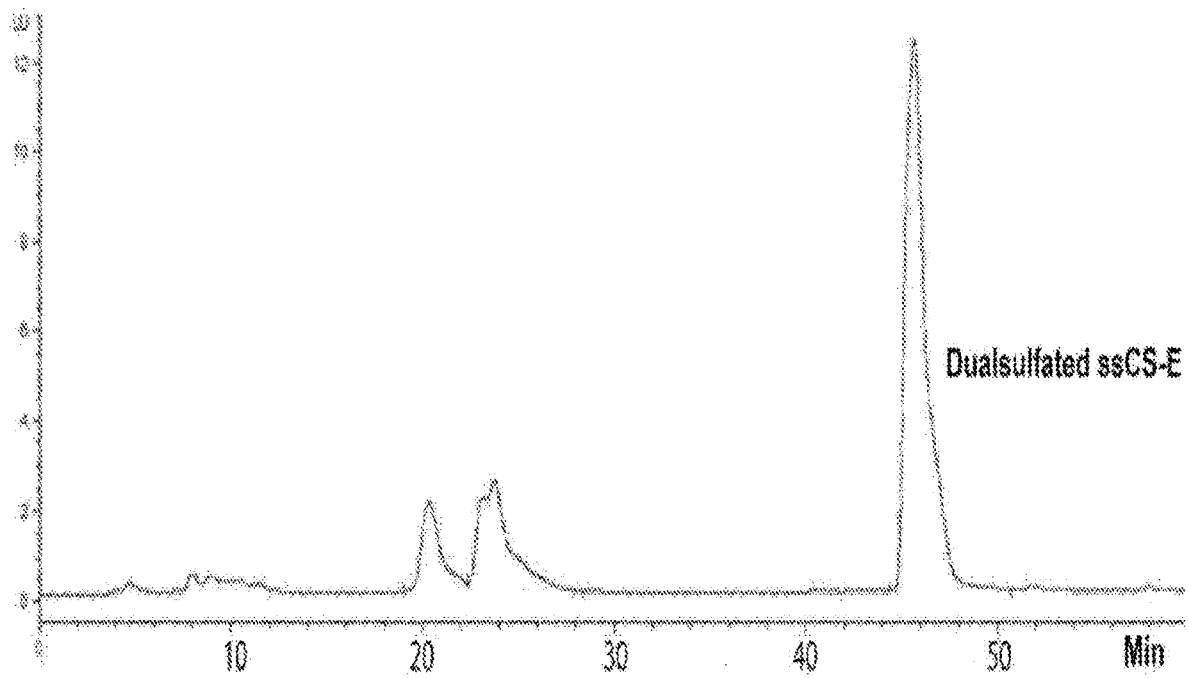

The monosulfated CS-A was used to synthesize the oversulfated mCS-E as described previously (Cai, C. et al., Carbohydr Polym, 2012, 87:822-829). The CS-A/C was dissolved in formamide, and trimethylamine sulfur trioxide was added to the solution. The reaction was heated to 60° C. and allowed to proceed for 24 hours with vigorous stirring under an argon blanket. Afterward, 95% aqueous ethanol was added and the mixture was held at room temperature for 30 minutes. To modify the reaction conditions, 1% aqueous NaCl was added, and the pH was adjusted to 7 with 2M NaOH. After dialysis, the solution was lyophilized to yield crude sulfated product. The crude product was dissolved in 16% aqueous NaCl and ethanol was added. After centrifugation at 4000 rpm, the pellet was re-suspended in deionized water and the solution was dialyzed. The percentage conversion of CS-A to semisynthetic CS-E (ssCS-E) was confirmed using strong anion exchange HPLC (SAX-HPLC) as described previously (Karumbaiah, L. et al., Bioconjug Chem, 2015, 26:2336-2349), and as depicted in FIG. 9. The dialysate was then lyophilized, and the CS-E was methacrylated using the same procedure as described for the methacrylation of monosulfated MeCS-A. The composite CS-A/E gels used in cell assays were 2% w/v CS-A with 15% CS-E, 0.05% Irgacure-2959 in DMEM/F-12, and exposed to 365 nm UV light.

Unsulfated high-molecular-weight hyaluronic acid from rooster comb (Sigma Aldrich, MO) was dissolved in DI water and autoclaved for 1 hour to partially hydrolyze the hyaluronic acid to low-molecular-weight HA. The resulting HA was then dialyzed against water for two days, and the dialysate was frozen at −80° C. and lyophilized for three days. The resulting HA was methacrylated according to the same procedure used to methacrylate CS-A as described above. The resulting mHA was reconstituted in DMEM/F-12 as 0.5% w/v HA with 0.05% Irgacure-2959, before exposure to 365 nm UV light.

Scanning Electron Microscopy (SEM)

The microarchitecture of lyophilized hydrogels was observed using a Zeiss 1450EP scanning electron microscope (Zeiss, NY). Hydrogels were cast in a tissue cryopreservation mold, flash frozen in liquid nitrogen, then lyophilized for 24-48 hours. Lyophilized gels were mounted on 10 mm stubs and sputter coated with gold for 60 seconds in a Module Sputter Coater (SPI, PA) before being imaged at 20 kV. Images were acquired at 500× and 1000× magnifications to observe the pores and structure of hydrogels. ImageJ software was used to calculate pore size based on 500× images.

Rheological Testing of Photocrosslinked mCS, mHA and Agarose Hydrogels 1 mL hydrogels made with deionized water were crosslinked by exposure to 365 nm UV exposure within tissue cryopreservation molds to yield hydrogels of ~3 mm thickness. The gels were cut into 16 mm diameter disks with a biopsy punch and left to incubate in 1 mL of PBS overnight at 37° C. to fully swell before rheological testing. Rheological testing on hydrogels was performed using a parallel plate rheometer (Anton Paar, CA). Frequency sweep experiments were done in triplicate from 0.1-100 Hz at 5% strain at 37° C.

Cell Culture

U87MG-EGFP human-derived glioblastoma cells were cultured in media consisting of DMEM/F-12 (Corning, NY) supplemented with 10% fetal bovine serum (Corning, NY), and 1% penicillin-streptomycin, incubated at 37° C. in a 5% CO2. Cells were fed with supplemented media every other day unless passaged or extracted for use in assays.

Cell Viability Assays $5 \times 10^5$ U87MG-EGFP cells were encapsulated into hydrogels and left in incubation for 48 h before being stained with Calcein Blue AM (Thermo Fisher, MA) according to manufacturer's instructions. Live cells emitting blue fluorescence were compared to GFP-expressing live or dead cells, and to brightfield images of the cells. Images were analyzed using a Leica DM IRB series microscope (Leica Microsystems, Inc., IL). Cell viability was assessed using colocalization of Calcein blue fluorescence to GFP green fluorescence in 20× images for at least four images per hydrogel sample, using cell colocalization tools associated with Volocity software (PerkinElmer, MA).

Microfluidics Device Fabrication and Preparation

Figures 10A, 10B:
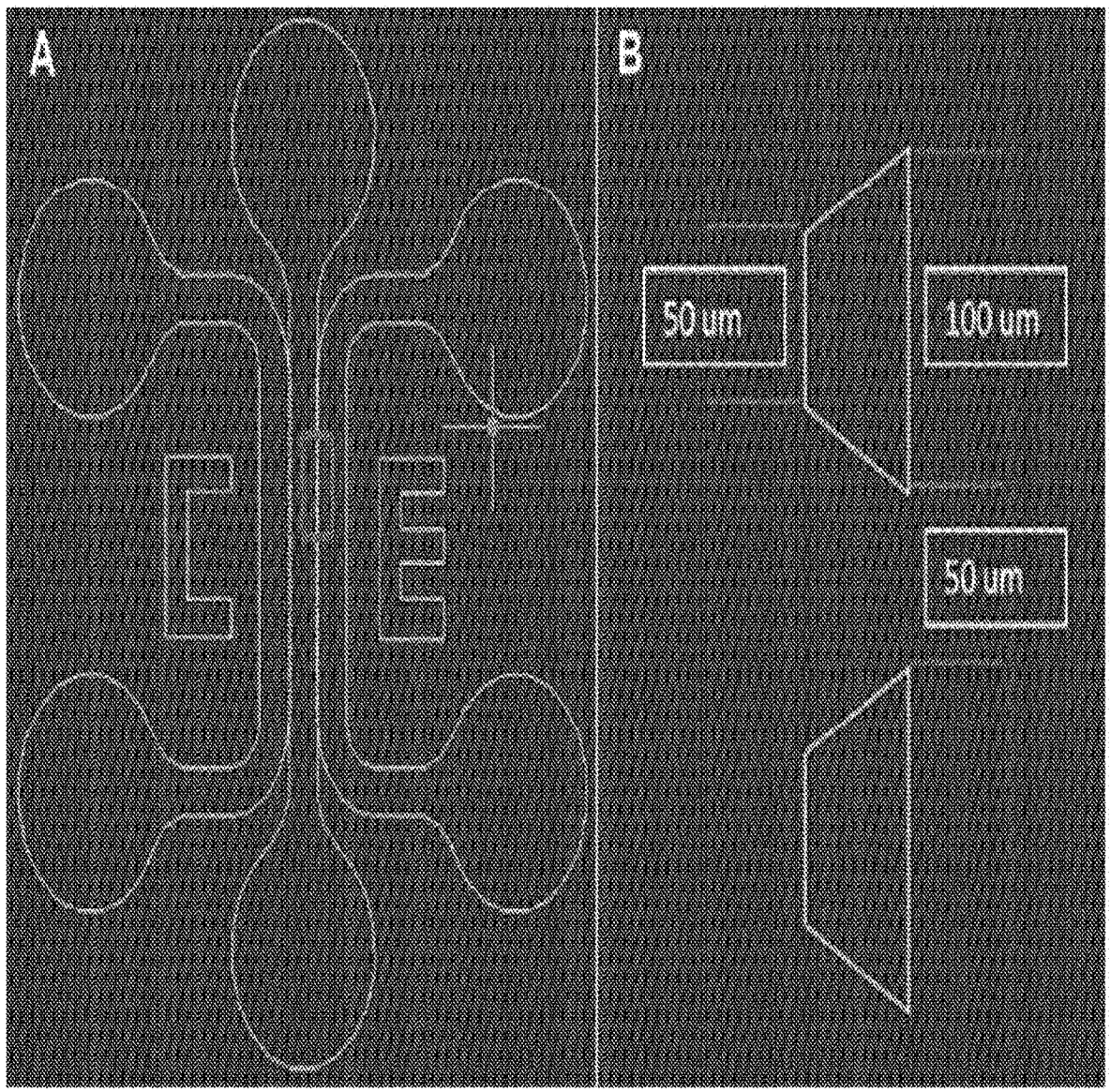
FIGS. 10A and 10B show autoCAD-generated schematic of the silicon wafer mold design used in fabricating the microfluidics devices for in vitro experiments.

The microfluidic device was fabricated through standard soft-lithography methods using polydimethylsiloxane (PDMS) in a 10:1 weight ratio with curing agent (Dow Corning, MI). Device pattern was designed after a previously described microfluidic platform to study tumor cell intravasation with minor modifications (Zervantonakis, I. K. et al., Proc Natl Acad Sci USA, 2012, 109:13515-13520). A mask of the device pattern was created using AutoCAD and printed by a commercial photo-plotting company (CAD/Art Services, OR). After cross-linking the polymer for 2 hours at 72° C., and punching the wells with a 4 mm biopsy puncher (Miltex, Inc., PA), device surfaces were bonded with a microscope cover glass after plasma surface treatment (Harrick Plasma, NY) with 18 W power for 30 seconds at 11.2 Pa $O_2$ partial pressure. Each device had three microfluidic channels with trapezoidal barriers between channels. The shape and dimension of channels was chosen to accommodate the quantification of cell choice and migration. Each channel was 10 mm in length and 1000 μm in width with 5 mm wells in diameter. Thickness of the device was measured to be 150 μm by a profilometer (Veeco Instruments Inc., PA). 300 μm trapezoidal barriers lined the junctions where two channels meet, with 100 μm spaces between barriers, to keep hydrogel constituents within the seeded channels and to restrict cell influx into adjacent channels (FIG. 10). Each device was coated in poly-D-lysine (PDL) overnight (Sigma Aldrich, MO), then baked at 80° C. for 48 hours to restore hydrophobicity. Devices were then kept at 4° C. until use.

U87MG-EGFP Encapsulation and Cell Migration Studies

Individual 14 mm glass-bottom cell culture dishes were used for sandwich cell encapsulations for viability study. Bilayer hydrogels were made from either 0.5% agarose (SeaPlaque, Lonza, NJ), 2% mCS-A, 2% mCS-A/E (2% COMP) or 0.5% mHA (all dissolved in DMEM/F-12). Cells were cultured as described above and 50,000 cells were encapsulated in each hydrogel. The mCS-A, mCOMP, and mHA were combined with 0.05% photocrosslinker before being exposed to 365 nm UV light for 45 seconds each. All assays were done in triplicate. Encapsulated cells were fixed at 24 hours using 4% paraformaldehyde in 0.4 M sucrose solution. Immunohistochemistry was performed to evaluate cellular production of focal adhesion kinase and vinculin. Cells were Hoechst-stained before encapsulation and are GFP-expressing. Imaging was done using a Leica DM IRB series microscope (Leica Microsystems, Inc., IL).

To evaluate cell migration through microfluidics devices, choice assays were designed to evaluate cell preference between two different hydrogels. Hydrogels were seeded into the side wells of the devices and gentle suction was used to pull the gel through the channel. Once gels filled the respective channel, they were either allowed to cool (agarose) or exposed to UV light for 15-20 seconds (mCS-A, mCS-A/E or mHA). U87MG-EGFP cells in media were Hoechststained and then 20,000 cells were seeded into the middle channel of the devices, using gentle suction to pull the cells in media all the way through the channel and not disturb the side channels full of hydrogels. Devices were then left for 6 hours to allow cells time to migrate and were imaged at the 6 hour time point using wide field epifluorescence imaging using a Leica DM IRB series microscope (Leica Microsystems, Inc., IL). All assays were performed in triplicate. Tiled images were taken using 10× magnification and quantifications were performed using Volocity software (Perkin Elmers, MA) to analyze migrating cells moving through only the hydrogel-laden channels and ignoring the middle cell culture channel. Inserts were taken at 20× magnification. Devices were fixed using 4% paraformaldehyde in 0.4 M sucrose solution. Staining for Focal Adhesion Kinase (FAK) and Vinculin was done using two-part antibody staining (Thermo Fisher, MA). Staining for F-actin polymerization was performed using Texas Red-X Phalloidin (Thermo Fisher, MA).

Haptotaxis Assays

Prior to conducting the CXCL12 haptotaxis assays, the uniform diffusion of the chemokine through the different hydrogel matrices was ascertained. In order to accomplish this, sulfated and unsulfated hydrogel matrices were cast in the microfluidic devices as described above and incubated with a 50 μl solution of PBS containing 10 ng/ml of Alexa Fluor 488-conjugated aprotinin, which has the same molecular weight as CXCL12. The diffusion of fluorophore conjugated aprotinin through the different sulfated and unsulfated hydrogels matrices was quantified at the end of 0, 3, and 6 h post-introduction and the fluorescence intensity quantified using methods described below.

The microfluidics platform was subsequently used to evaluate cell haptotaxis in response to CXCL12 presence. Each hydrogel type was tested in three microfluidics devices, where the same hydrogel was placed into both side channels with one side receiving 10 ng/mL CXCL12 (R&D Systems, NE) and the other side receiving media only. 20,000 cells in media were seeded into the middle channel. Devices were imaged at zero, three, and six hours to evaluate cellular haptotaxis response across AG, HA, CS-A and COMP hydrogels. Tiled images were taken using 10× magnification on a Leica DM IRB series microscope and quantifications were performed using Volocity software to analyze migrating cells moving through the hydrogel-laden channels. Devices were fixed using 4% paraformaldehyde in 0.4 M sucrose solution. Proof of a chemokine gradient was established using Alexa Fluor 488-conjugated Aprotinin (Thermo Fisher, MA and Sigma Aldrich, MO respectively) at zero, three, and six hours using Volocity software to calculate fluorescence within the channels of the microfluidics devices.

Sandwich ELISA

Binding to immobilized CS-A and COMP was done using a sandwich ELISA assay. The wells in the 96-well NeutrAvidin-coated plate (Thermo Fisher, MA) were washed with 1×PBS, then were blocked with 1% BSA in 1×PBS for one hour. After another wash step, biotinylated GAGs were added in a 1:10 ratio in PBS to each well and left overnight at 4° C. Control wells received no GAGs, only PBS. Next day the plate was blocked with 1% BSA, 5% sucrose, and 0.05% Tween 20 in PBS for one hour. After a wash step, 0-200 nM concentrations of CXCL12 (R&D Systems, ND) were added on top of each treatment for one hour. After a wash step, a 1:100 dilution of anti-CXCL12 antibody (R&D Systems, ND) in PBS was added to wells for two hours. Wells were washed, then a 1:50 k dilution of HRP conjugated secondary antibody (R&D Systems, ND) was added. Another final wash step was done, TMB Buffer (Thermo Fisher, MA) was added and after 30 minutes 2M sulfuric acid was added as stop solution to measure absorbance of the plate at 450 nm.

Western Blotting 100 k U87MG-EGFP cells were encapsulated in 2% CS-A, 2% COMP, 0.5% HA or 0.5% AG hydrogels, along with a media only control cultured as described above for 72 h. Cell lysates were extracted using 1× Mammalian Protein Extraction Buffer (GE Healthcare Life Sciences, PA) containing cOmplete ULTRA protease inhibitor cocktail (Sigma Aldrich, MO). 50 μg of total cell lysate protein each obtained from glioma cells subjected to media only (M), AG, HA, CS-A, and COMP treatments were resolved through a 4-20% gradient gel (Bio-Rad Mini Protean TGX Gels, CA), and subsequently transferred to pure nitrocellulose membranes (Osmonics Inc, MN). After transfer, blots were allowed to dry for two hours, then rehydrated in 1×TBS for 2 min. Membranes were blocked for 1 h with Odyssey TBS Blocking Buffer (LI-COR, NE), then placed in primary antibody solution containing the primary antibody, Odyssey TBS Blocking Buffer, and 0.02% Tween-20 and left at 4° C. overnight with gentle shaking. Primary antibodies used include: anti-CXCL12 (R&D Systems, NE), anti-CXCR4 (Thermo Scientific, CT), anti-LAR (BD Biosciences, CA), and anti-GAPDH (Abcam, MA). After removing primary antibody solution, membranes were washed with Odyssey TBS Blocking Buffer+0.02% Tween-20, then overlaid with Odyssey TBS Blocking Buffer+0.02% Tween-20 containing Odyssey TRDye 680RD (LI-COR, NE) for 1 h. Membranes were then washed with 1×TBS+0.02% Tween-20, and then 1×TBS. Membranes were kept in 1×TBS until imaging using the LI-COR Odyssey CLx at 700 nm.

qRT-PCR

Total RNA was isolated using RNeasy Plus Mini kit (Qiagen, CA) from cells encapsulated in 2% CS-A, 2% COMP, 0.5% HA or 0.5% AG hydrogels after 72 h. Following genomic DNA elimination (Qiagen, CA) and following manufacturer protocol, cDNA was synthesized using the RT First Strand kit (Qiagen, CA). A total of 100 ng total RNA equivalent of cDNA template was used in 25 μL qRT-PCR reactions for each group along with SYBR green dye (Qiagen, CA), and primers targeting human CXCL12 (CXCL12, PPH00528B, NM_000609), human CXCR4 (CXCR4, PPH00621A, NM_001008540), and LAR (LAR, PPH02317F, NM_002840); and the endogenous housekeeping genes GAPDH and HPRT1 (GAPDH, PPH00150F, NM_001256799; HPRT1, PPH01018C, NM_000194), and amplified using a ABI 7900HT machine (Applied Biosystems, CA) using conditions described previously (Karumbaiah, L. et al., Bioconjug Chem, 2015, 26:2336-2349; Karumbaiah, L. et al., Glia, 2011, 59:981-996). Each sample was assayed in triplicate for both target and endogenous controls using cycle conditions: 95° C. for 10 minutes, 40 cycles of 95° C. for 15 seconds, and 60° C. for 1 minute followed by a melting curve analysis. Relative quantitative gene expression was appraised using the ΔΔCT method. The levels of the target gene expression was calculated after normalization to media-only control and against endogenous controls for each sample and then presented as relative units. A greater than 2 fold increase in expression of CXCL12, CXCR4, or LAR when compared to media-only controls was considered significant.

Statistical Analysis

For all migration and haptotaxis experiments, precise cell counting, fluorescence quantification, and colocalization protocols were used in Volocity software to analyze raw data. All analyses for across-group variation were performed using one-way analysis of variance (ANOVA) for significance ($p<0.05$) with appropriate post-hoc tests using SigmaPlot software. Direct mean comparisons were evaluated using t-tests. All studies were performed in triplicate at the minimum.

Results

Figure 1B:
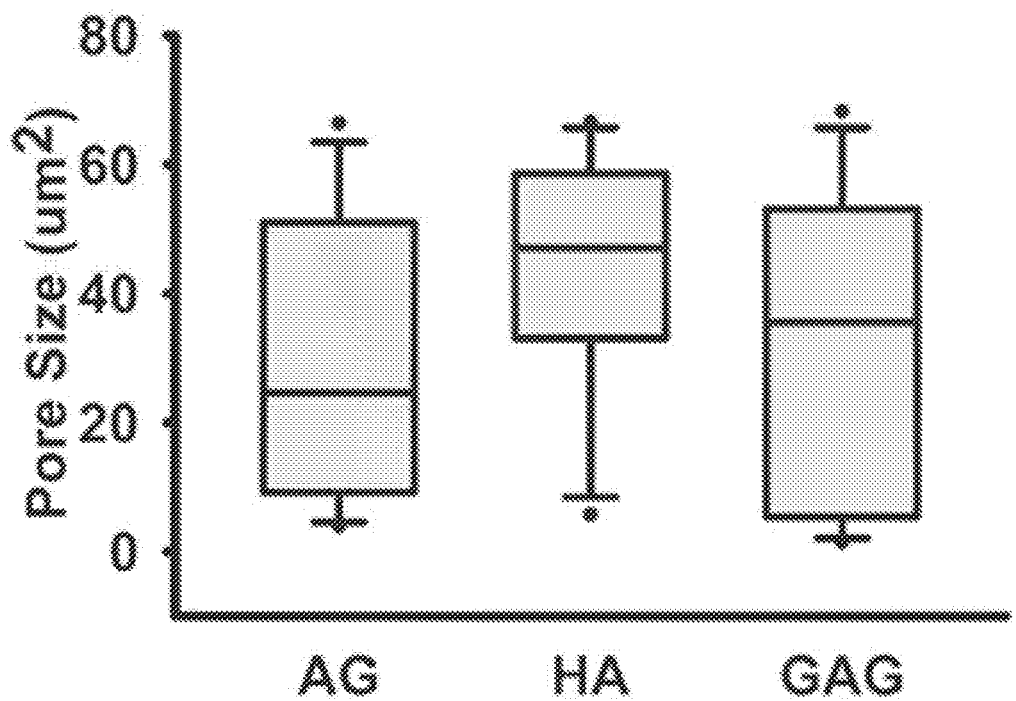
Figure 1C:
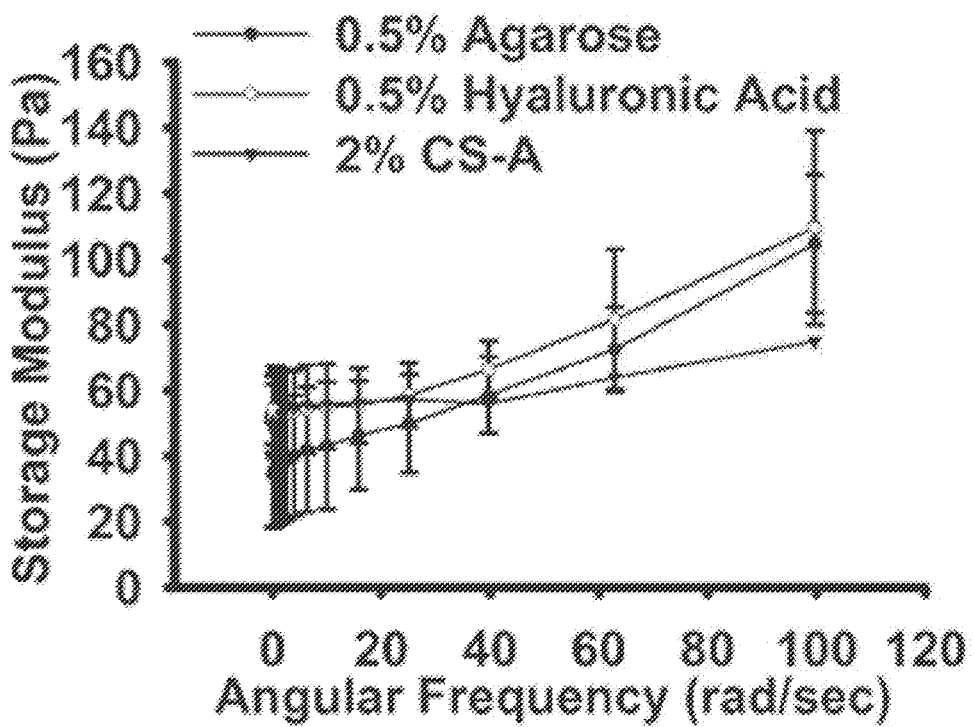
Figure 2:
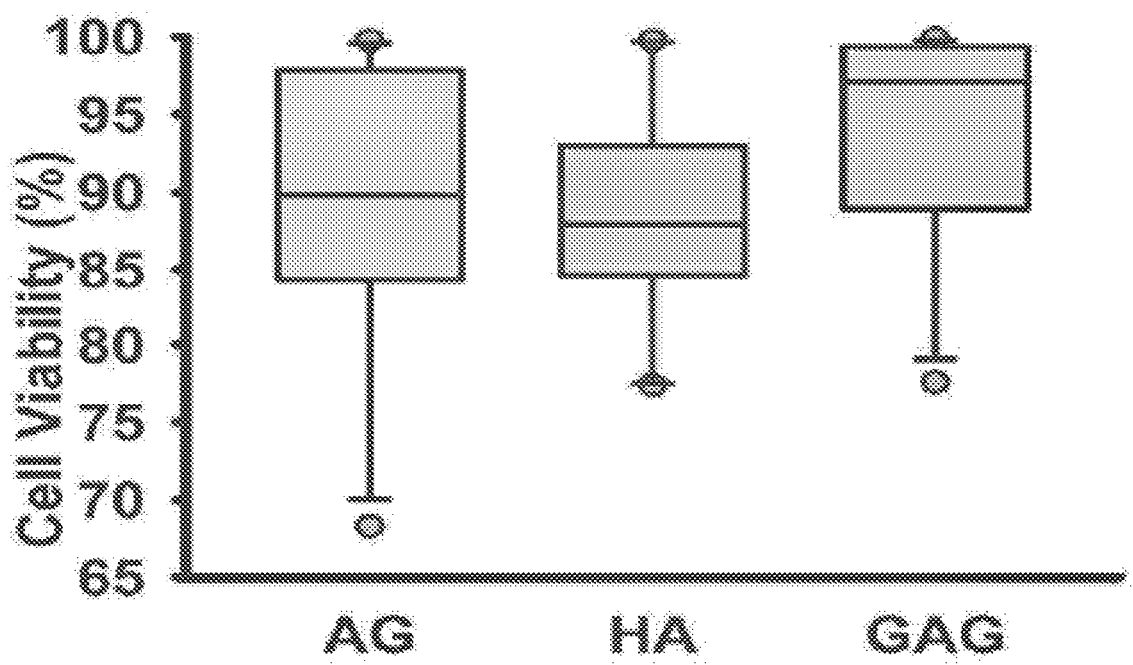
FIG. 2 shows viability assessment of cells encapsulated into different hydrogel matrices, as determined by a Calcein Blue AM assay 48 h post-encapsulation. Representative 20×GFP/Calcein Blue and 20×GFP/Calcein Blue/Brightfield images of cells encapsulated in 0.5% AG, 0.5% HA, and 2% CS-A hydrogels. Scale bar=50 μm. No significant differences in % live cells were observed between the three groups, as determined by a one-way ANOVA.

Biomechanically Optimized Hydrogel-Based Brain ECM Mimics Facilitate the Assessment of Glioma Cell Behavior In Vitro In order to evaluate glioma cell behavior in response to specific ECM components, and to prevent the confounding effects of varying biomechanical properties of hydrogel-based ECM mimics on cell behavior, rigorous characterization of hydrogel porosity and elastic modulus was performed. 0.5% (w/v) agarose, 0.5% (w/v) hyaluronic acid and 2% (w/v) monosulfated CS hydrogels demonstrated similar pore sizes, with the average pore size ranging between 25 and 45 $\mu m^2$ (FIGS. 1A & 1B). The hydrogel types tested displayed comparable storage moduli across a standard angular frequency sweep range of 0-100 rad/sec (FIG. 1C). The storage moduli obtained for the different hydrogel types tested were comparable to that of CNS tissue, which can range in storage modulus between <100 to a few hundred Pascal (Lu, Y. B. et al., Proc Natl Acad Sci USA, 2006, 103:17759-17764). The U87MG-EGFP glioma cells encapsulated in AG, HA and CS hydrogels demonstrated a mean survival of ~85% as indicated by the calcein blue+ cells co-expressing GFP 48 h post hydrogel encapsulation (FIG. 2).

Figure 3A:
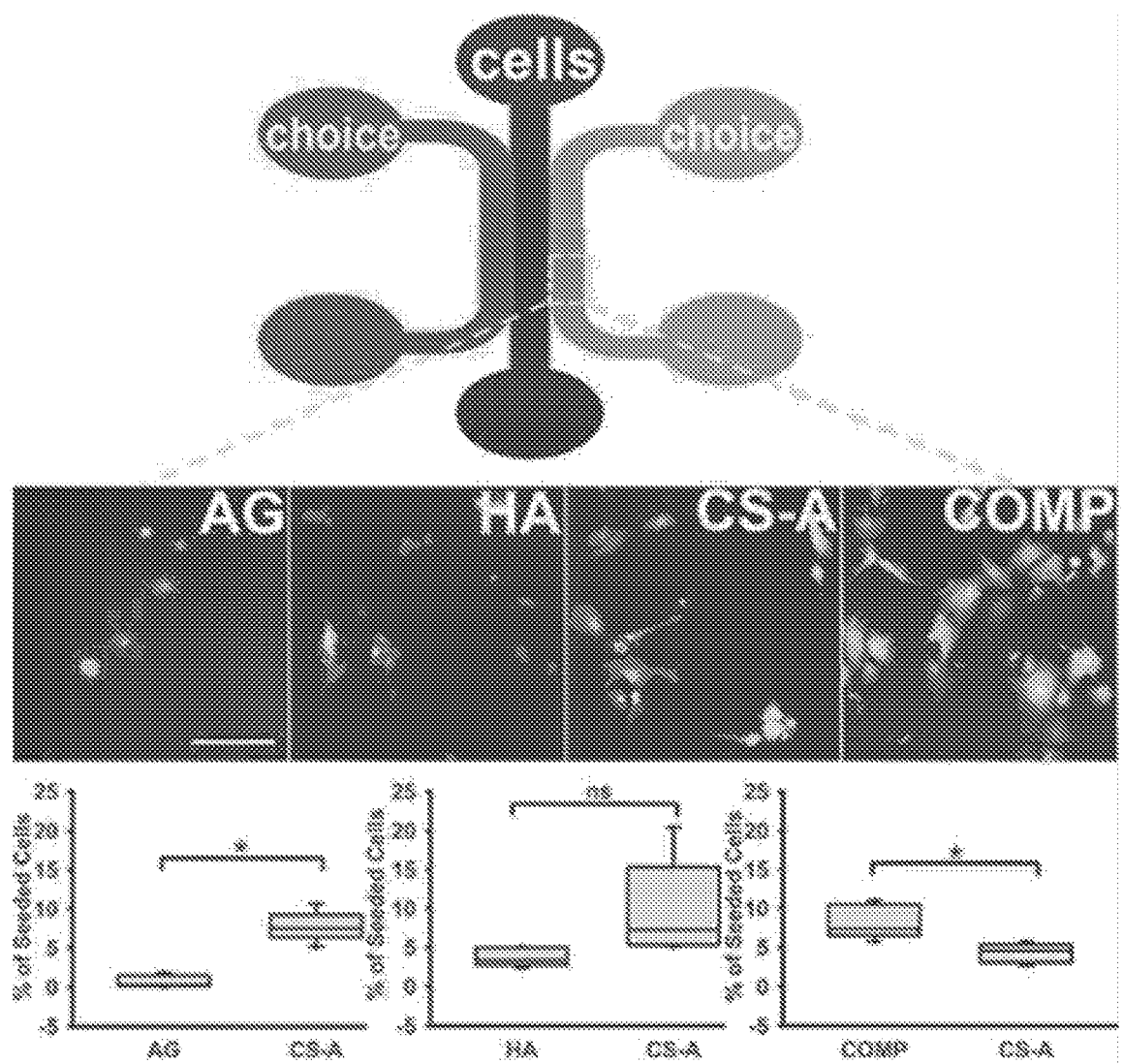
FIGS. 3A, 3B, and 3C show microfluidics-based evaluation of cellular preference of hydrogel environment.
Figures 3B, 3C:
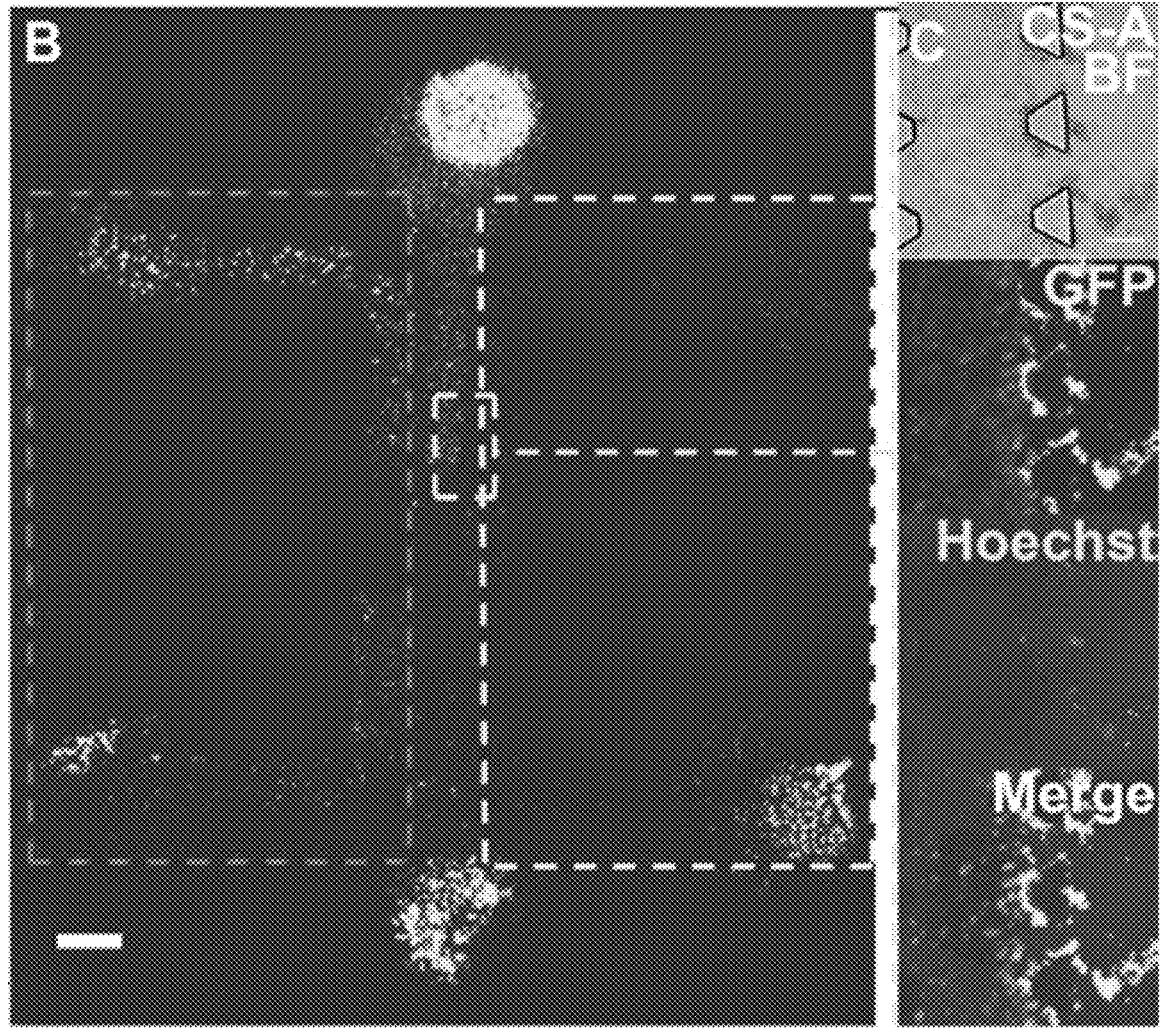
Figure 4A:
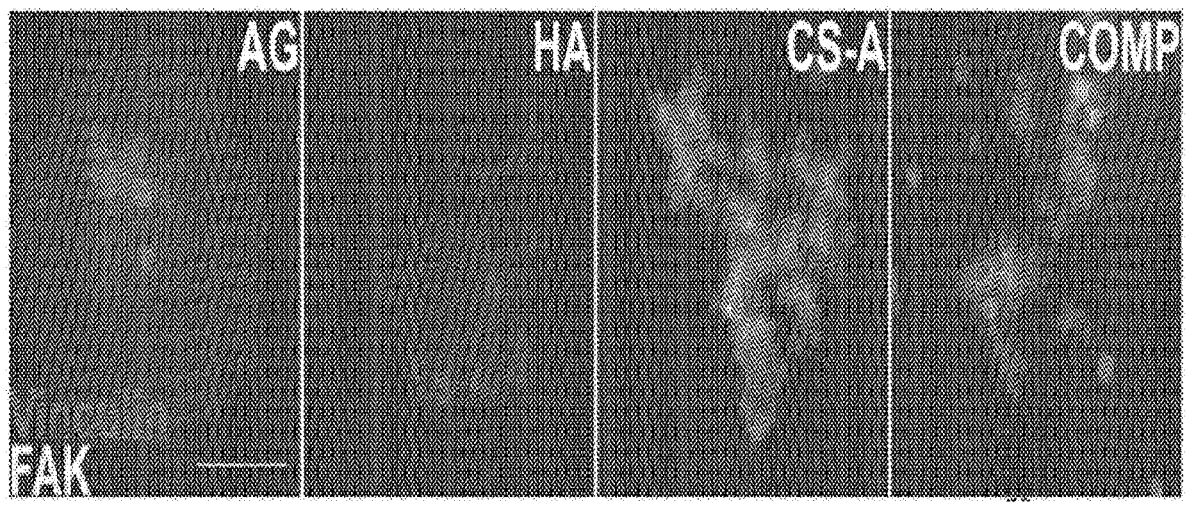
FIGS. 4A, 4B, 4C, and 4D show immunocytochemical staining of encapsulated glioma cells within microfluidics devices 6 h post cell-seeding.
Figure 4B:
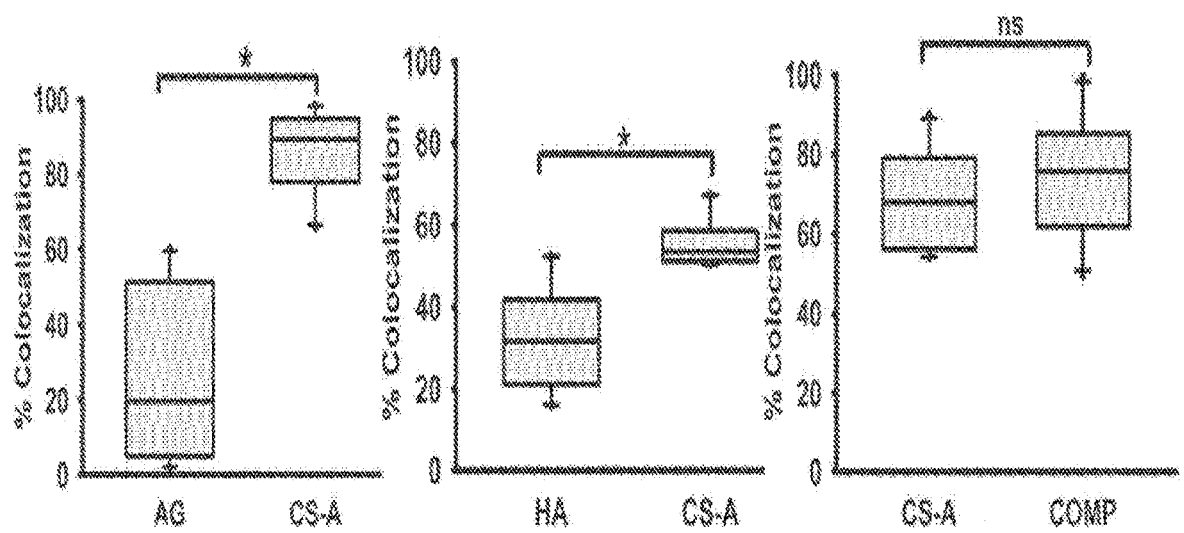
Figure 4C:
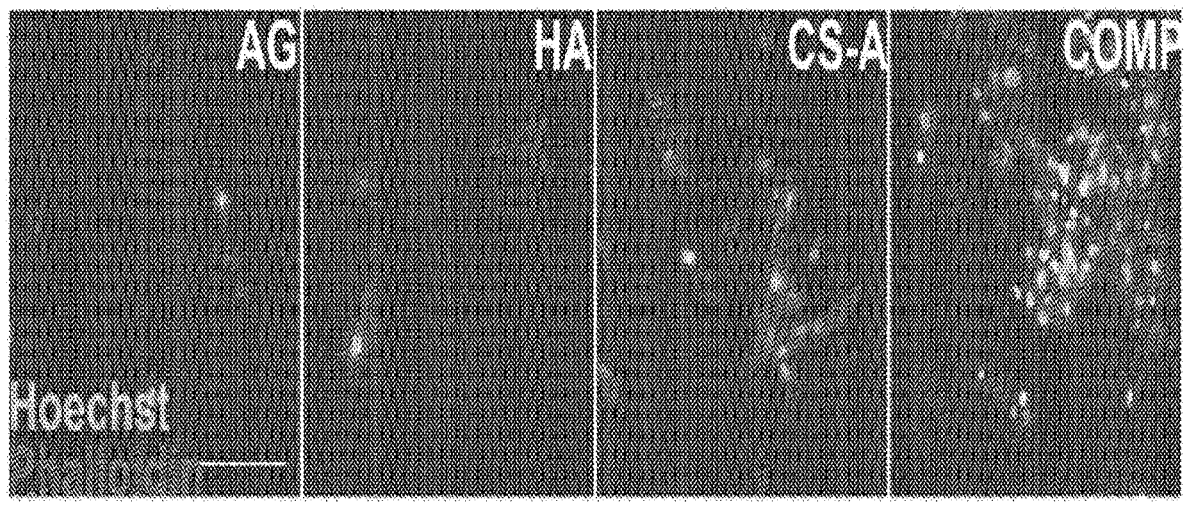
Figure 4D:
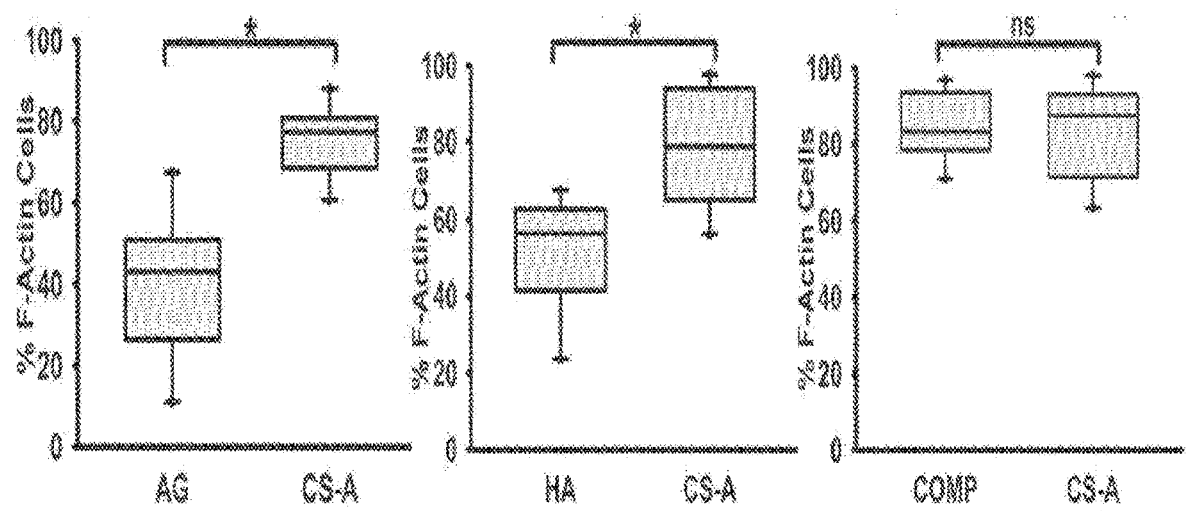
Figure 11:
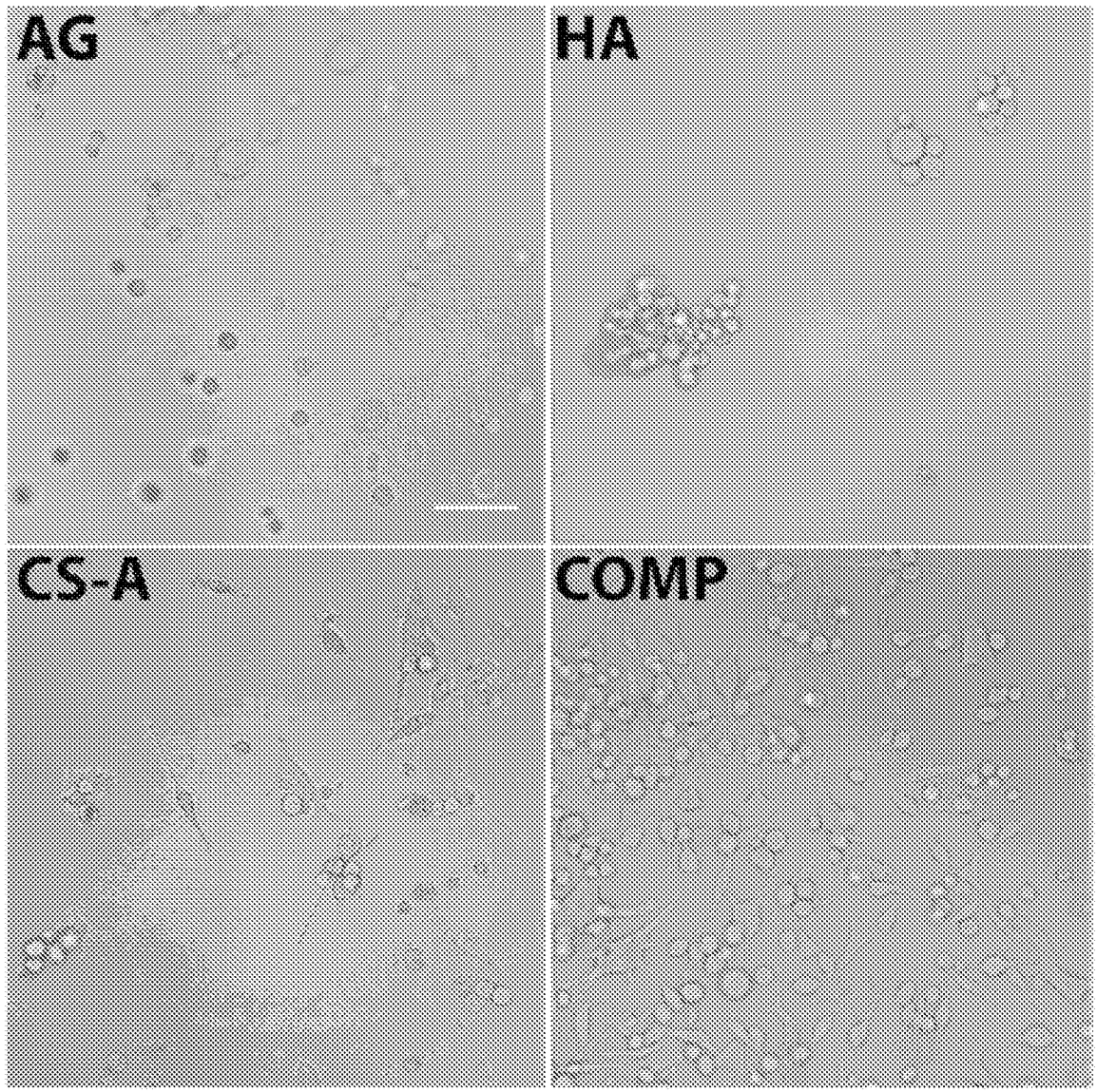
FIG. 11 shows representative brightfield images of U87MG-EGFP cells within AG, HA, CS-A, and COMP hydrogel matrices displaying differential cell morphology. Images were acquired 48 h post-encapsulation. Scale bar=50 µm.

U87MG Cells Demonstrate Significantly Greater Infiltration into Sulfated CS-GAG Hydrogels when Compared to Other Hydrogel Matrices To assess the glioma cell preference for sulfate-rich environments, the design of a three channel microfluidics platform was modified as described below to present U87MG cells seeded in the central channel with a "choice" between a sulfated CS hydrogel, and an unsulfated hydrogel control (FIG. 3A). The number of cells in each of the two hydrogel types was quantified after 6 h, which represented the earliest time-point at which differences in glioma cell infiltration could be determined. Results from these assays demonstrate that a significantly greater percentage ($p<0.05$) of glioma cells infiltrated into sulfated CS-GAG hydrogels when compared to either unsulfated AG or HA hydrogels (FIG. 3A). When a head-to-head comparison of monosulfated CS hydrogels to COMP CS hydrogels was conducted, a significantly greater ($p<0.05$) percentage of the seeded glioma cells were found to infiltrate into the COMP hydrogels when compared to the monosulfated CS hydrogels (FIG. 3A). Immunocytochemical analyses of the focal adhesion (FA) adaptor protein vinculin and FAK demonstrated that a significantly ($p<0.05$) higher percentage of glioma cells encapsulated in sulfated CS-GAG hydrogels showed a significantly ($p<0.05$) higher percentage of colocalization of these cytoskeletal proteins when compared to unsulfated AG or HA hydrogels (FIG. 4B). No-significant differences in the expression of these proteins was observed in glioma cells encapsulated in monosulfated CS-A hydrogels when compared to composite CS hydrogels (FIG. 4B). A significantly higher ($p<0.05$) percentage of glioma cells encapsulated within the sulfated CS-GAG hydrogels demonstrated the presence of polymerized filamentous actin (F-actin) when compared to cells encapsulated in unsulfated AG or HA hydrogels (FIG. 4D). No significant differences in F-actin polymerization were observed when glioma cells encapsulated in monosulfated CS-GAG hydrogels were compared to those encapsulated in COMP CS-GAG hydrogels (FIG. 4D). In conjunction with increasing cytoskeletal remodeling, the morphology of cells encapsulated in CSGAG hydrogels displayed increasing cytoplasmic prolongations into the surrounding 3D matrix (FIG. 11).

The Immobilization of CXCL12 in CS-GAG Hydrogels Enhances U87MG Cell Haptotaxis

Figure 5A:
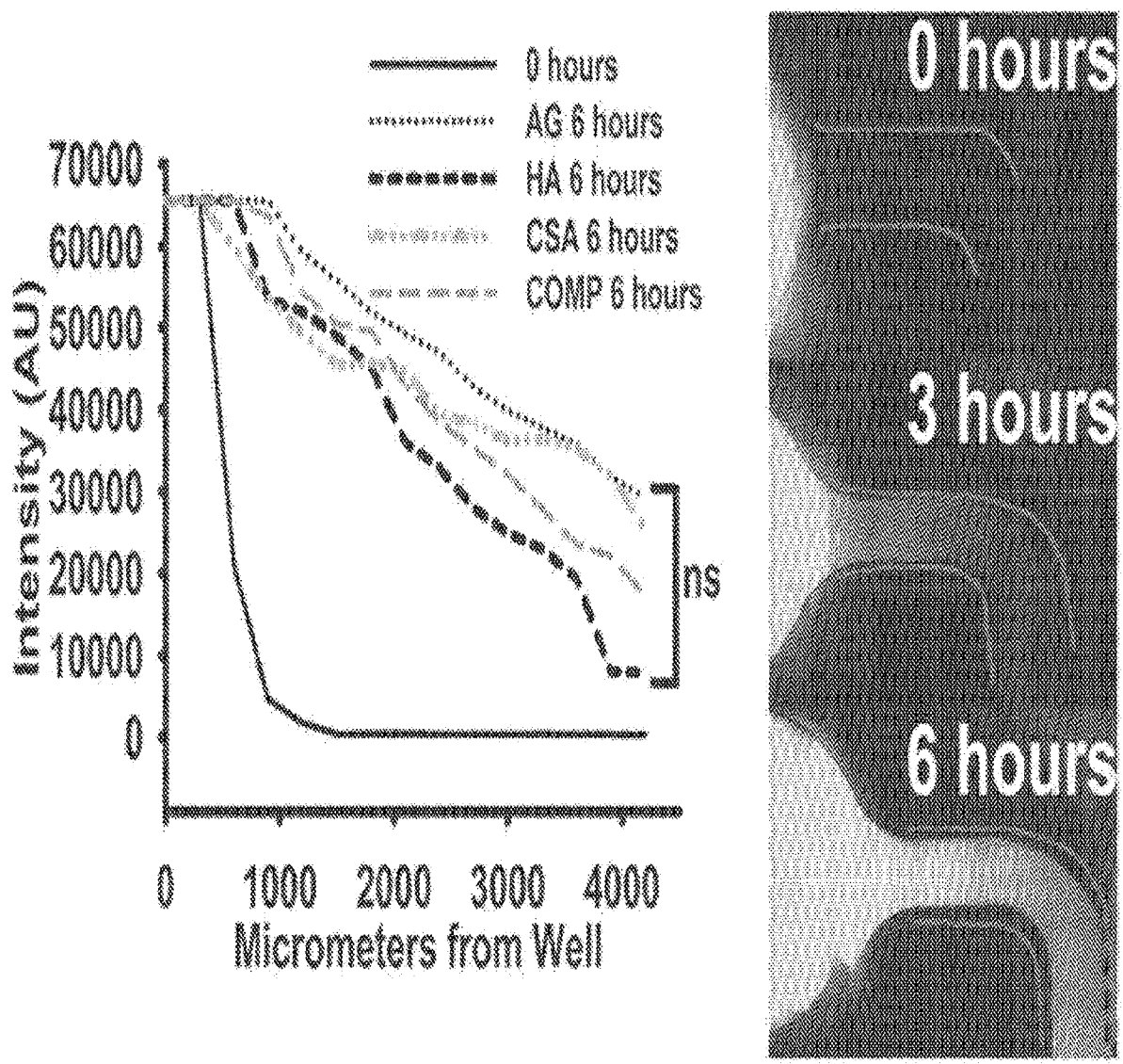
FIGS. 5A and 5B show haptotaxis of cells in response to matrix immobilized CXCL12 presence.
Figure 5B:
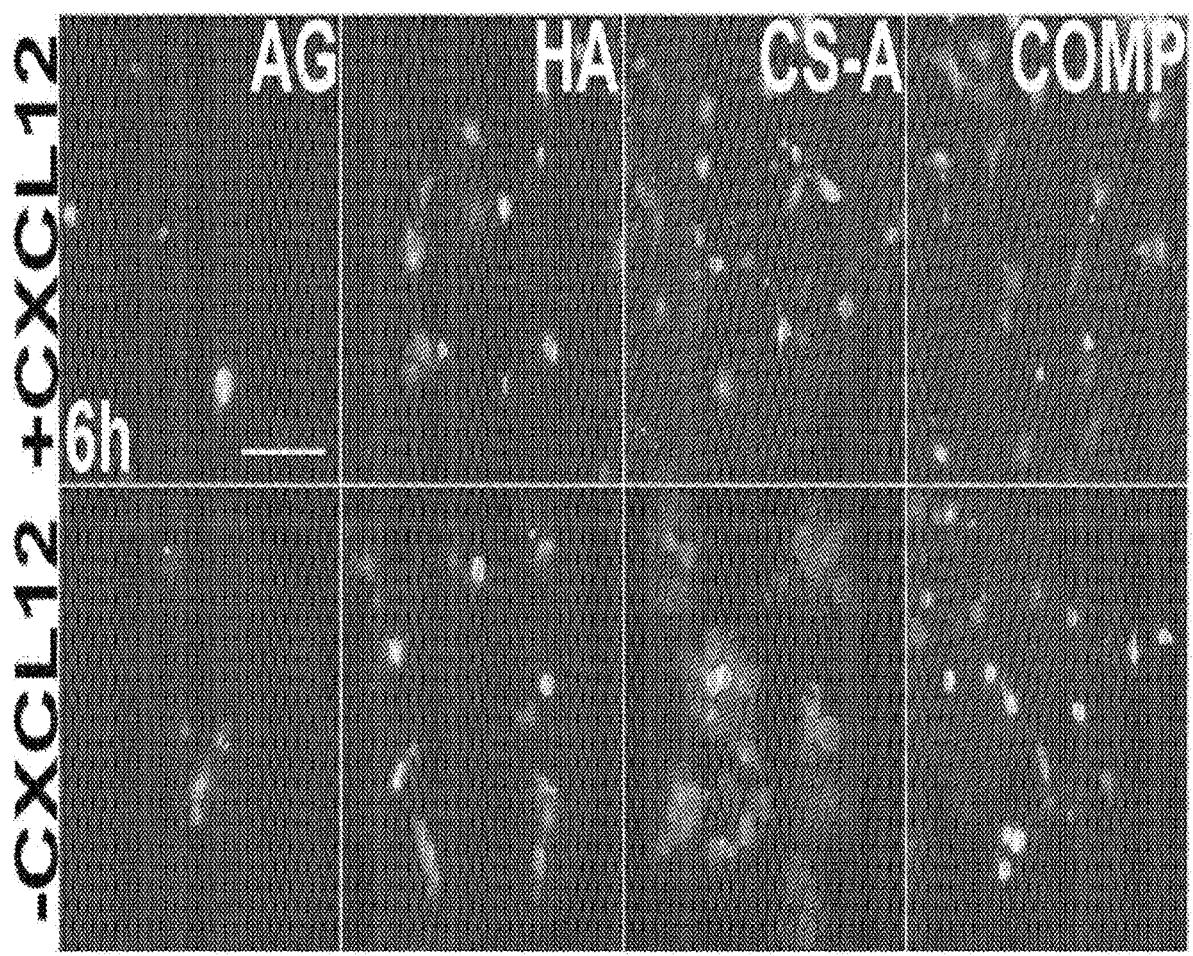
Figure 6:
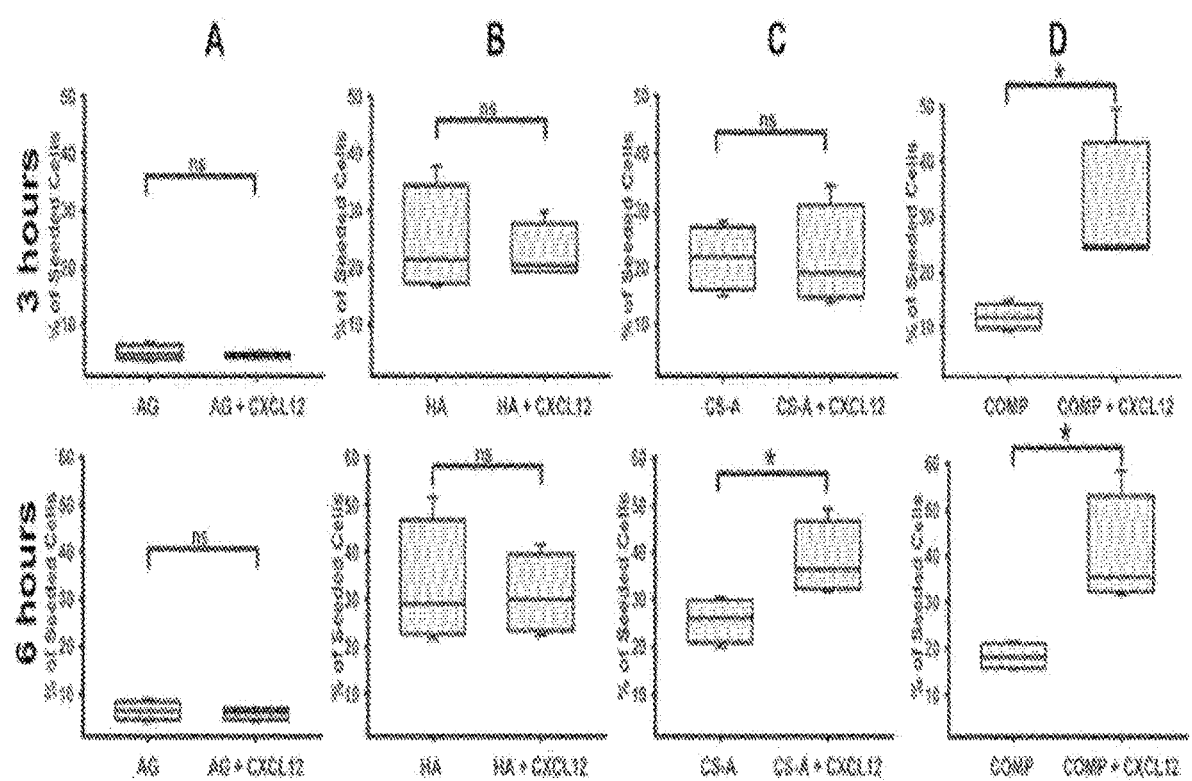
FIG. 6 shows the quantification results of haptotaxis in hydrogel matrices with and without 10 ng/mL CXCL12 at three and six hours post-encapsulation within (A) AG, (B) HA, (C) CSA, and (D) COMP hydrogels. Data are represented as mean+SD, and means with '*' (p<0.05) are significantly different from other treatments.

The microfluidics platform described above was used to assess protein diffusion and subsequently the haptotaxis of glioma cells encapsulated in hydrogels, both in the presence and absence of 10 ng/mL CXCL12. Results from the protein diffusion assays demonstrate the steady temporal increase in fluorescence intensity as a function of distance from the epicenter of the well across all hydrogel matrices. No significant differences in the extent of protein diffusion were observed across the different sulfated and unsulfated hydrogel matrices tested after 3 h and 6 h (FIG. 5A). Subsequently, glioma cells were encapsulated in sulfated CS and unsulfated AG and HA hydrogels, and cellular haptotaxis in the presence and absence of 10 ng/mL CXCL12 was quantified. Glioma cells displayed the significantly enhanced infiltration ($p<0.05$) into COMP hydrogels containing CXCL12 over and above COMP hydrogels without CXCL12 at 3 h post cell-seeding. No significant differences were observed in cellular chemotaxis across other hydrogels ($p<0.05$) (FIGS. 5B & 6). At the 6 h time point, augmented cell migration was observed into both CXCL12-containing both CS-GAG hydrogels when compared to CS-GAG hydrogels without CXCL12 (C, D of FIG. 6). No significant differences were observed in haptotaxis of glioma cells encapsulated in other hydrogel types (A, B of FIG. 6).

CS-GAG Binding to CXCL12 is Sulfation Dependent

Figure 7A:
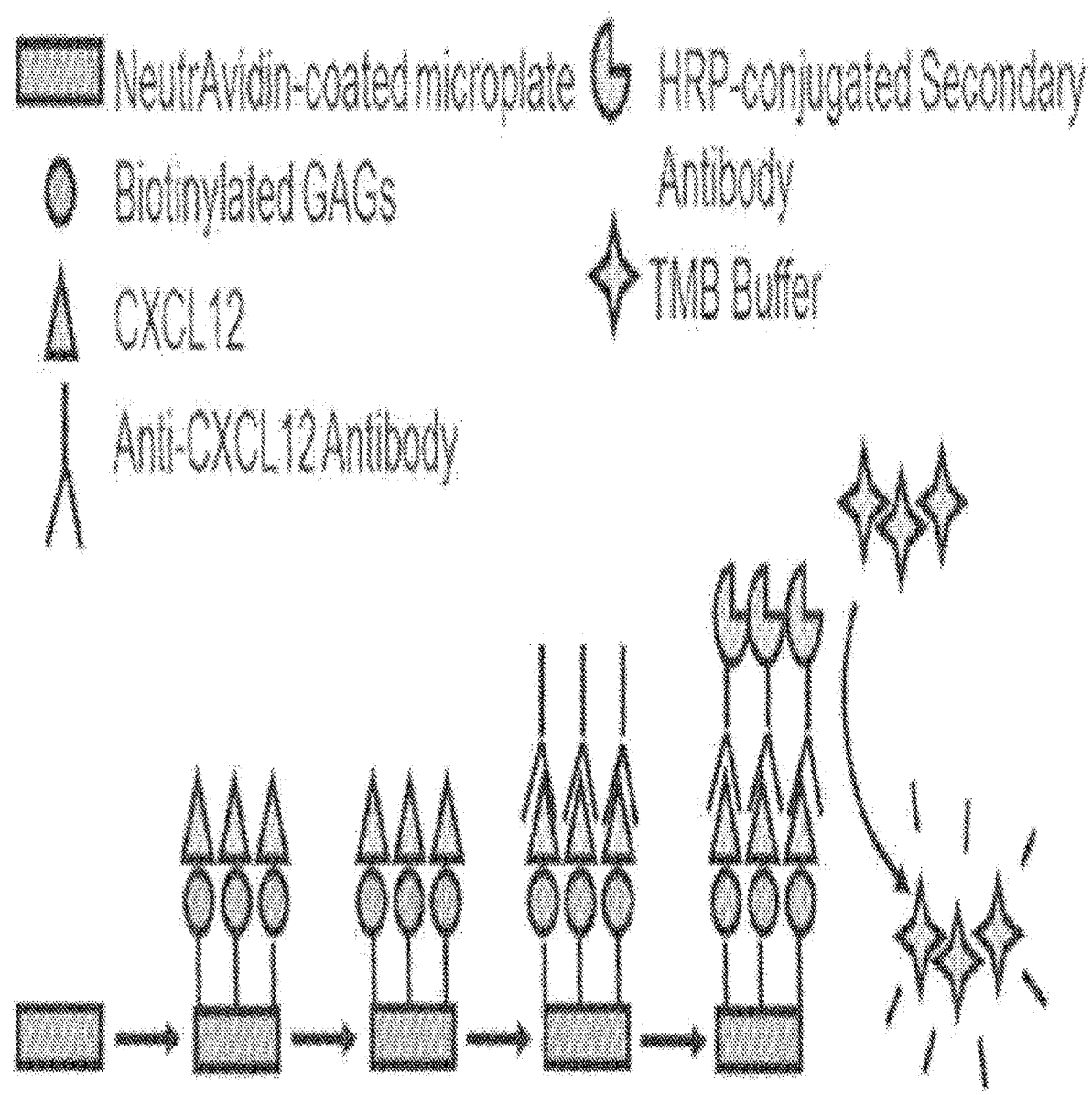
FIGS. 7A and 7B shows the binding of CXCL12 to immobilized GAGs as quantified by sandwich ELISA assay.
Figure 7B:
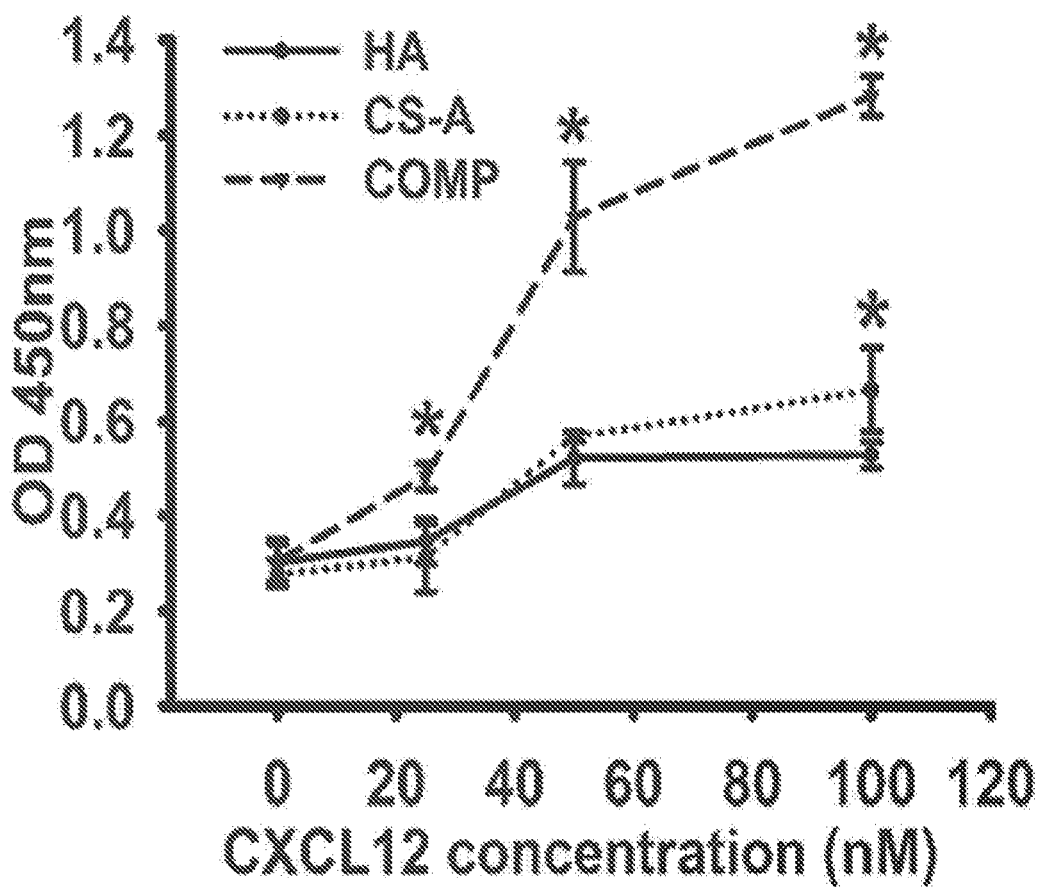

Sandwich ELISA binding assays were performed using a range of CXCL12 concentrations (0-100 nM) in order to evaluate the specific binding of CXCL12 to sulfated CS-GAGs and unsulfated HA. The immobilization of HA, monosulfated CS, and COMP GAGs, and subsequent detection of specific binding was performed according to methods described below and in FIG. 7A. Results from these assays demonstrate a significantly ($p<0.05$) greater concentration dependent binding of CXCL12 to COMP GAGs when compared to monosulfated CS-A or unsulfated HA across three of the four concentrations as indicated by the higher OD levels at these concentrations (FIG. 7B). There were no significant differences in CXCL12 binding to monosulfated CS-A when compared to HA in the lower three CXCL12 concentrations tested. However, a significant increase ($p<0.05$) in CXCL12 binding to monosulfated CS-A over unsulfated HA was observed at the highest concentration (100 nM) tested (FIG. 7B).

Figure 8A:
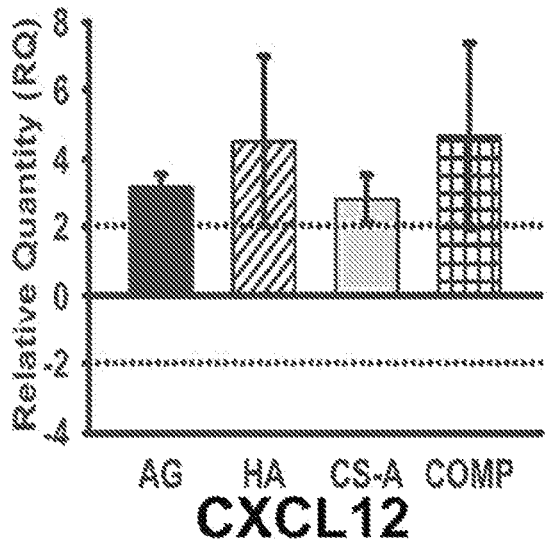
FIGS. 8A, 8B, and 8C show quantitative RT-PCR results demonstrating relative expression levels of (FIG. 8A) CXCL12, (FIG. 8B) CXCR4 and (FIG. 8C) LAR transcripts isolated from encapsulated cells. All fold changes were calculated relative to levels in media-only controls, and normalized against expression levels of housekeeping genes GAPDH and HPRT1. Data are represented as mean+SD, and means with '*' (p<0.05) are significantly different. A label of 'ns' demonstrates no significant difference.
Figure 8B:
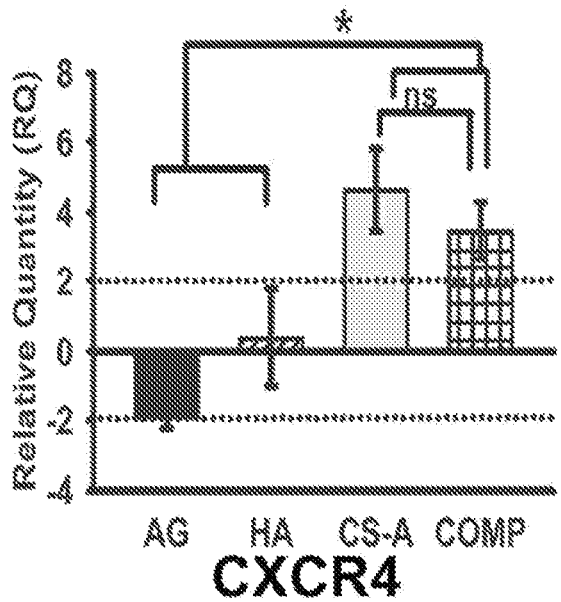
Figure 8C:
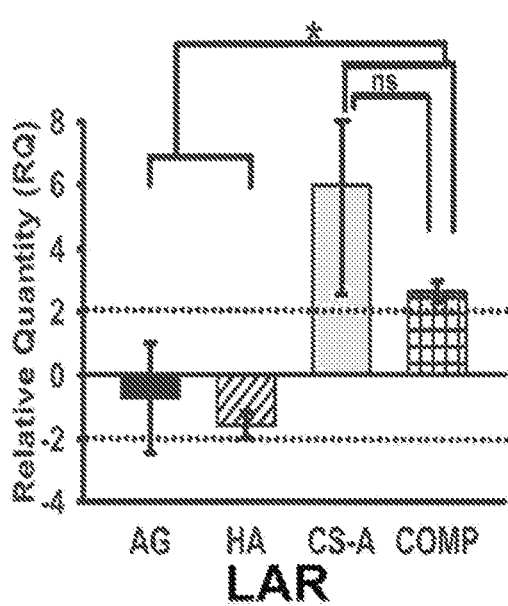
Figure 8D:
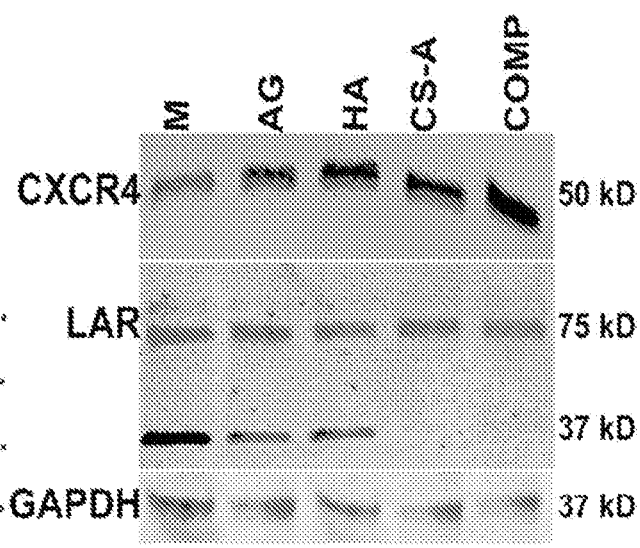
FIG. 8D shows western blot results confirming presence of extracellular CXCL12, as well as intracellular CXCR4 and LAR receptors across all hydrogel treatments and media-only control, compared to control protein GAPDH.

Glioma Cells Encapsulated in CS-GAG Hydrogels Demonstrate Enhanced Expression of the CXCR4 and LAR Transcripts In order to further elucidate the potential mechanisms contributing to the observed selective differential infiltration of glioma cells in the different sulfated CS-GAG, and unsulfated HA and AG hydrogels, the mRNA expression levels of CXCL12, CXCR4 and LAR were quantified in hydrogel encapsulated glioma cells 72 h post encapsulation using methods described below and as previously published (Valmikinathan, C. M. et al., Biofabrication, 2012, 4:035006). Results from these assays demonstrate the greater than two-fold upregulation of the transcript encoding CXCL12 in hydrogel encapsulated glioma cells across all hydrogel types, with no significant differences observed between groups (FIG. 8A). In contrast, glioma cells encapsulated in the sulfated CS-GAG hydrogels demonstrated a greater than two-fold increase, and a significantly greater ($p<0.05$) expression of transcripts encoding CXCR4 and LAR when compared to cells encapsulated in AG and HA hydrogels (FIGS. 8B & 8C). No significant differences in expression of these transcripts were observed between glioma cells encapsulated in either monosulfated CS or COMP hydrogels. Protein presence was validated through western blotting of both cell lysates and harvested media from hydrogel encapsulations after 72 h (FIG. 8D). No significant differences were observed in CXCL12 presence across cells encapsulated in different hydrogel matrices.

CONCLUSIONS

In summary, these results indicate that the heightened presence of extracellular CS-GAGs directly induces the enhanced cell migration and haptotaxis of glioma cells in a GAG sulfation dependent manner. The identification of the role of CS-GAGs in ECM-driven glioma behaviors would greatly advance understanding of glioma invasion, and contribute to the design of therapeutic interventions to help stem invasion. This study demonstrates that CS-GAG sulfation patterns could potentially mediate these outcomes by influencing cell membrane receptor expression and by selectively regulating chemokine presentation. The diffuse cellular invasion that characterizes glioblastoma multiforme is one of the biggest obstacles to successful treatment in the clinical setting, and though there is currently no effective treatment for malignant brain tumors, investigating the relationship between CS-GAGs and glioma invasion could help open doors for targeted therapy approaches to stem the invasive progression of these brain tumors.

TABLE 1

Estimated amounts (μg) and corresponding percentage (w/w) of chondroitin sulfate as determined by SAX-HPLC.

| | CS A/C | | ssCS-E | |
|---|---|---|---|---|
| CS | Mass | % | Mass | % |
| D0a0 | 0.319 | 2 | 0.038 | 1 |
| D0a6 | 2.35 | 13 | 0.504 | 17 |
| D0a4 | 15.9 | 85 | 0.557 | 19 |
| D2a0 | ND | | 0.028 | 1 |
| D2a6 | 0.020 | 0* | 0.023 | 8 |
| D0a10 | 0.092 | 0* | 1.54 | 52 |
| D2a4 | 0.051 | 0* | 0.045 | 2 |
| D2a12 | ND | | 0.562 | 19 |
| Total CS | 3.00 | 100 | 2.944 | 100 |

All values represent the amount estimated for total reaction volume.
Total analysis volume of sample = 100 μL, or 20 μg of starting material.
'ND' = Not Detected;
0* indicates a calculated value that is less than 1 percent.

Methods

Trophic Factor Enrichment in Sulfated CS and Unsulfated HA Matrices.

In order to assess the enhanced ability of CS-GAG matrices to bind and retain FGF2 when compared to HA matrices, they were cast into circular holes cut out from a ~1 mm thick HA matrix as described below. Methacrylated CS-GAG consisting of 86% CS-4 (CS-A), 5% 6 (CS-C), 6% 4,6 (CS-E) sulfated GAGs; and HA were synthesized. One mm thick HA matrices were cast in a 35 mm cell culture dish containing a 14 mm glass bottomed microwell (Cellvis, CA). ~1 mm round disks were cut out from the HA matrices using a biopsy punch, and the holes filled in with CS-GAG matrix and photo-cross-linked. The gels thus patterned were then overlaid with PBS containing 10 ng/mL FGF2, and incubated for 1 week in a standard humidified air incubator held at 37° C. and 95% humidity containing 5% $CO_2$. After 1 week, the PBS was removed from the gels, and the gels were frozen in optimal cutting temperature (OCT) compound (Sakura Finetek, CA). Frozen gels were later sectioned using a Leica cryostat (LeicaBiosystems, IL) at 15 μm thick sections. Sections were washed thrice with PBS and immunohistochemically stained with anti FGF2 primary antibody (Abcam, MA) and appropriate secondary antibody. Fluorescein labeled *Wisteria floribunda* agglutinin (WFA; Vector Laboratories, CA) was used to mark the location of the CS-GAG matrix. Fluorescently stained matrices were imaged using epifluorescence microscopy (Leica Microsystems, IL).

Surgical Procedures and TBI Induction.

All animals were approved by the Georgia Institute of Technology Institutional Animal Care and Use Committee (IACUC), and protocols were performed in accordance with the Guide for the Care and Use of Laboratory Animals published by the National Institute of Health (NIH). A total of 45 seven-week-old Sprague-Dawley (~200 g) rats were obtained from Harlan Laboratories and assigned to control and experimental groups. Nine animals served as sham controls, receiving a craniotomy but no CCI injury. The remaining 30 six animals were evenly divided into the positive control TBI group (TBI), the CS-GAG matrix implant group (GAG), the NSC injection group (NSC), and the combined CS-GAG-NSC matrix implant group (GAG-NSC). A custom-designed CCI was used to deliver the desired impact to the frontoparietal cortex of the TBI-only control and experimental animals. Prior to injury, each rat was anesthetized using 5% isoflurane gas and the head was then depilated to expose the underlying skin. The animal was then placed on a heated pad to maintain its body temperature at 37° C., and its head was mounted into a stereotaxic frame (David Kopf Instruments, CA) with the nose placed into a nose mask that delivered the aforementioned level of surgical anesthesia. The surgical site was sanitized thrice using alternating chlorhexidine and ethanol swabs. A longitudinal incision was made such that bregma, coronal, sagittal, and lambdoid sutures were exposed. The skin flaps and tissue was reflected on either side of the incision, and a 5 mm craniotomy was performed 0.5 mm anterior to bregma and 0.5 mm lateral from the sagittal suture using a 5 mm diameter trephine bur and an electronic drill. The bone flap was subsequently removed, noting any blood, hemorrhages, and the state of dura. A 3 mm tip attached to the pneumatic piston of the CCI was extended to its full length and positioned near the surface of the exposed dura in the top right corner of the craniotomy. The piston was retracted and lowered 2 mm, then fired at a velocity of 2.25 m/s and with a dwell time of 250 ms, resulting in a 3 mm diameter injury with a depth of 2 mm. A saline soaked piece of gelfoam was applied to the injury site, and sterile cotton swabs were used to remove any excess blood. The gel foam was subsequently removed, and the injury site was covered completely with a layer of 2% SeaKem agarose (Lonza, MD). The skin flaps were subsequently sutured together to close the wound, and triple antibiotic cream was layered on top of the sutured skin. Buprenorphine (1 mg/kg) was injected subcutaneously before animals were removed from anesthesia and placed in a new, clean cage under a heating lamp to recover. The animals were returned to their home cages after recovery.

NSC Culture.

Primary rat NSCs isolated at embryonic day 14 (MTIGlobalStem, MD) were subcultured in ES-DMEM-F12 (MTIGlobalStem, MD) containing N2 supplement and 10 ng/mL FGF2. The cultures were maintained in a standard humidified air incubator held at 37° C. and 95% humidity containing 5% $CO_2$, and culture media was replaced every 2 days. After approximately 3-4 days when plates reached about 90% confluence, cells were rinsed thrice using 20 mM HEPES Buffered Salt Solution (HBSS) lacking calcium or magnesium (Corning, NY) and scraped from the culture dish using a cell scraper to detach the cells. The detached cells were centrifuged at 270 g for 5 min and the pellet was resuspended in ES-DMEM/F12. The cells were counted using an automated cell counter (Bio-Rad, CA) and prepared for encapsulation and delivery as described below.

Intraparenchymal Injection of Matrices and Matrix Encapsulated NSCs.

Two days post-TBI, injured animals were randomly assigned to either the positive control TBI group (n=9) or one of the three experimental groups GAG, NSC, or GAG-NSC (n=9 per group). CS-GAG matrices with or without PKH26GL (SigmaAldrich, MO) labeled NSCs were photo-cross-linked on the day of injection. In the case of animals receiving NSCs only, ~300 000 PKH26GL labeled rat NSCs were resuspended in basal media (20 μL volume), and delivered using methods below. For animals receiving CS-GAG matrix-only controls, 20 μL of 3% w/v CS-GAG matrix in neurobasal media containing 0.05% photoinitiator (Irgacure-2959, Sigma-Aldrich, MO) was backfilled into a 50 μL Luer Lock (TLL) Hamilton syringe fitted with a BD Visitec Nucleus Hydrodissector needle (BD Medical, NJ). The solution was subsequently cross-linked in the syringe by exposing it to 365 nm long wavelength UV light (160 W BlakRay UVP, CA) for 30 s and prepared for intraparenchymal delivery as described below. For animals receiving NSC laden CS-GAG matrices, 300 000 NSCs were resuspended in 20 μL 3% (w/v) methacrylated CS-GAG in neurobasal media containing 0.05% photoinitiator (Irgacure-2959) and back-loaded into a 50 μL Hamilton syringe as described above and prepared for delivery as described below.

The animals were prepared for intraparenchymal injections by placing them under surgical anesthesia as described above. The incision area was sanitized using ethanol and chlorhexidine as described above, and the sutures were removed to reflect the skin flaps. The 2% agarose matrix was carefully removed from the injury site using sterile saline soaked cotton swabs, without disturbing the underlying brain tissue. For each treatment containing NSCs only, CSGAG only, or GAG-NSCs, the syringe was fitted onto a syringe pump and assembled on an electrode manipulator (David Kopf, CA) at a 32° angle. The needle tip was then implanted in the injury epicenter to a depth of 2 mm. A 20 μL volume of the matrix was delivered at a rate of 2 μL per minute, over a period of 10 min using the syringe pump. After 10 min, the needle was held in place for 5 min and then gradually retracted. The surface of the cortex was kept moist with a piece of gel foam soaked in saline during the course of this procedure. The gelfoam was subsequently removed, and the craniotomy was overlaid with 2% agarose as described above and covered with UV curing dental cement. The skin flaps were sutured and the animal was allowed to recover as described above.

Neural Tissue Preparation and Immunohistochemistry.

Four weeks postinjury, animals were heavily sedated using ketamine (65 mg/kg) and transcardially perfused with 250 mL PBS (pH 7.4) followed by 250 mL of 4% paraformaldehyde in PBS, and finally with 100 mL 20% sucrose in PBS. The brains were then extracted and cut at the epicenter of the lesion using a rat brain matrix (Ted Pella Inc., CA) to result in two halves. Each half section was frozen fresh first in liquid nitrogen and then stored at −80° C. The extracted brains were sectioned at 15 µm thickness using a cryostat (LeicaBiosystems, IL), collecting 10 slides per animal (5 slides from the rostral side of the injury and 5 from the caudal side). Immunohistochemical staining of cryostat sectioned brain slices was performed using primary and secondary antibody pairs as described in Table 2.

TABLE 2

List of Immunohistochemical Markers

| Target | Antibody |
| --- | --- |
| Neurons | Neu N |
| Neurons | NF200 |
| Astrocytes | GFAP |
| Macrophages | CD68 |
| NSCs | Sox1 |
| NSCs | Nestin |
| Proliferating cells | Ki67 |
| Oligodendrocytes | Olig2 |
| Fibroblast growth factor | FGF2 |
| N-acetylgalactosamine (GalNAc) residues linked to CS-GAGs | FITC-WFA |

Brain sections collected on glass slides, were rinsed in PBS and subsequently incubated in PBS containing 4% paraformaldehyde and 0.4 M sucrose for 30 min. The slides were then assigned to primary antibody groups and incubated for 1 h in blocking buffer (PBS containing 4% goat serum and 0.5% Triton-X100), followed by overnight incubation in blocking buffer containing appropriate antibodies (Table 2). The following day, the slides were washed several times in PBS at room temperature and exposed to blocking buffer for 1 h at room temperature. Slides were then incubated with blocking buffer consisting of 1:220 dilutions of appropriate secondary antibodies for 1 h. Following incubation, slides were washed several times in PBS. 500 µL NucBlue (Life Technologies, NY) in PBS was added to each slide for 5 min at room temperature. Slides were rinsed thrice with PBS and coverslipped using Fluormount-G (Southern Biotech, AL). Sections were allowed to cure overnight, and stored at −20° C. until imaged.

Nissl bodies in brain sections were stained using cresyl violet stain (SigmaAldrich, MO). Sections were placed in PBS containing 4% paraformaldehyde containing 0.4 M sucrose for 30 min. The fixed sections were rinsed thrice in PBS, and air-dried following which they were immersed in a 1:1 solution of alcohol and chloroform. The next day, the sections were sequentially rehydrated through 100%, and 95% EtOH, and finally into DiH2O. The sections were subsequently labeled with 0.1% cresyl violet solution for 5-10 min to stain for Nissl bodies in neurons. The stained sections were cleared by passing them sequentially through DiH2O, 70, 95, and 100% EtOH. The dehydrated sections were finally cleared in xylene and coverslipped with permount temperature.

Quantification of Immunofluorescence.

Cresyl violet stained slides marking nissl bodies were imaged at the coronal epicenter of the injury using a light microscope (Nikon bright field and Q-Imaging software). The region of interest (ROI) represented 10.494 mm$^2$, and four images were taken per animal (n=9; 36 total images). ImageJ was used to determine and analyze the number of marked nissl bodies, thresholding to signal peak (~200) and using the subtraction tool to eliminate any noise. For immunofluorescent slides, five sections spanning the injury site were imaged using epifluorescence microscopy (LeicaBiosystems, IL), and fluorescence staining intensity was quantified using Volocity (PerkinElmer, MA). The Manders overlap coefficient was used to measure the degree of overlap and colocalization between dual-colored fluorescent images, as it is a better indicator of co-occurrence when compared to other methods. It is represented by the equation:

$$\frac{\sum_i (R_i X G_i)}{\sqrt{\sum_i R_i^2 X \sum_i G_i^2}}$$

Where $R_i$ and $G_i$ are the fluorescence intensity values of the red and green channels in a pixel "i", respectively.

Statistical Analysis.

All statistical inferences for CS-GAG enrichment and immunohistochemical assays were made using SigmaPlot (SyStat Software, Inc., CA). Student's t-test, one way analysis of variance (ANOVA), and a one-way repeated measures ANOVA on ranks with multiple pairwise comparisons and relevant posthoc tests were applied as deemed appropriate. For all tests, $p < 0.05$ was considered significant.

Results

FGF2 Retention in CS and HA Matrices.

Figure 12A:
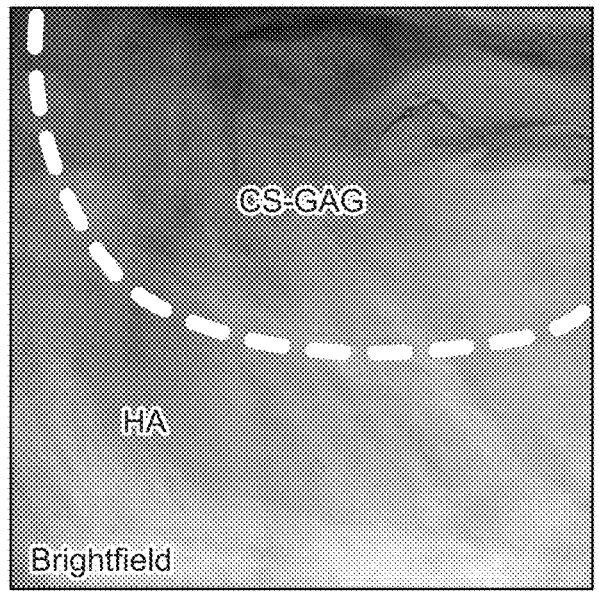
FIGS. 12A, 12B, 12C, and 12D show selective binding and retention of FGF2 to ~1 mm diameter CS-GAG matrix surrounded by HA matrix.
Figure 12B:
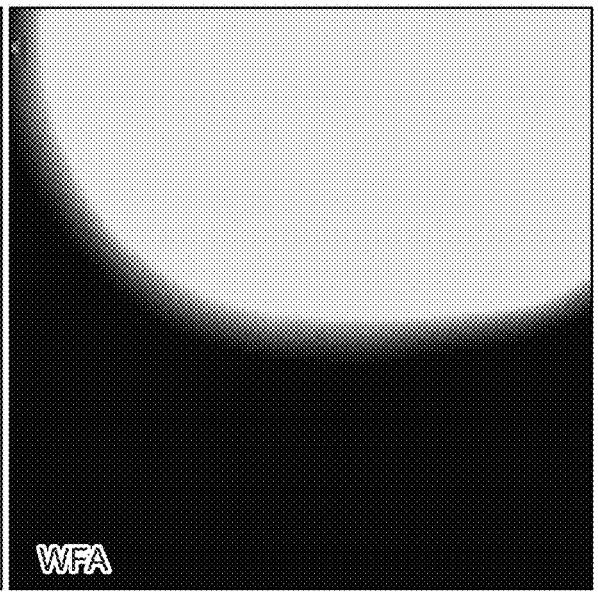
Figure 12C:
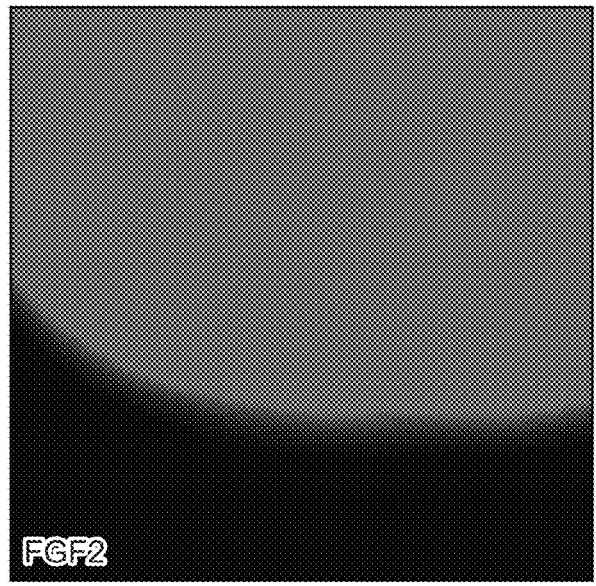
Figure 12D:
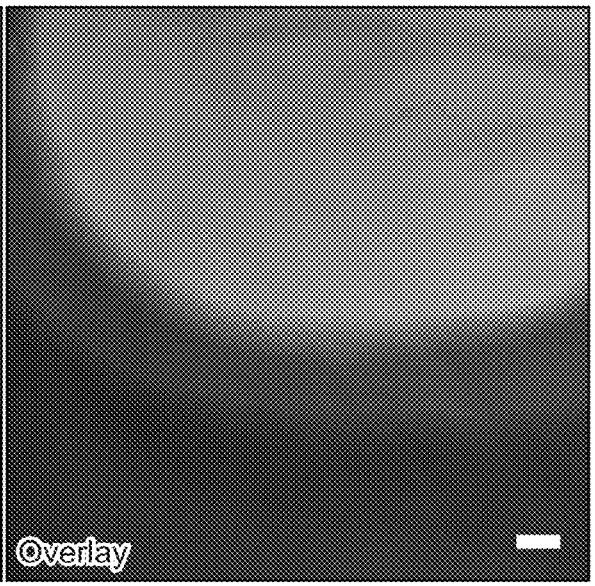
Figure 13A:
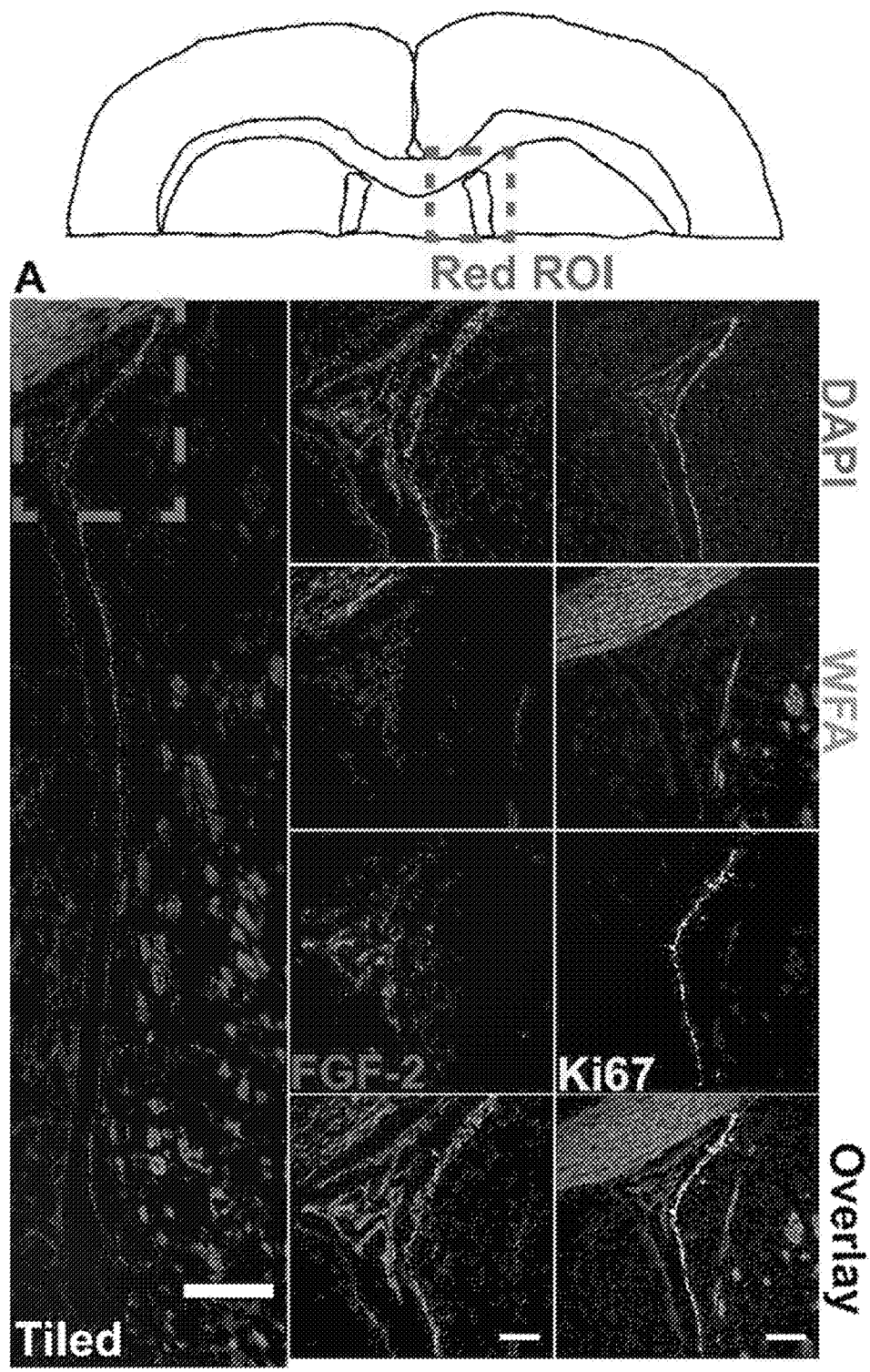
FIGS. 13A, 13B, 13C shows coronal rat brain section demonstrating the colocalization of CS-GAGs, FGF-2 and Ki67+ proliferating cells in the rat subventricular zone (SVZ).
Figures 13B, 13C:
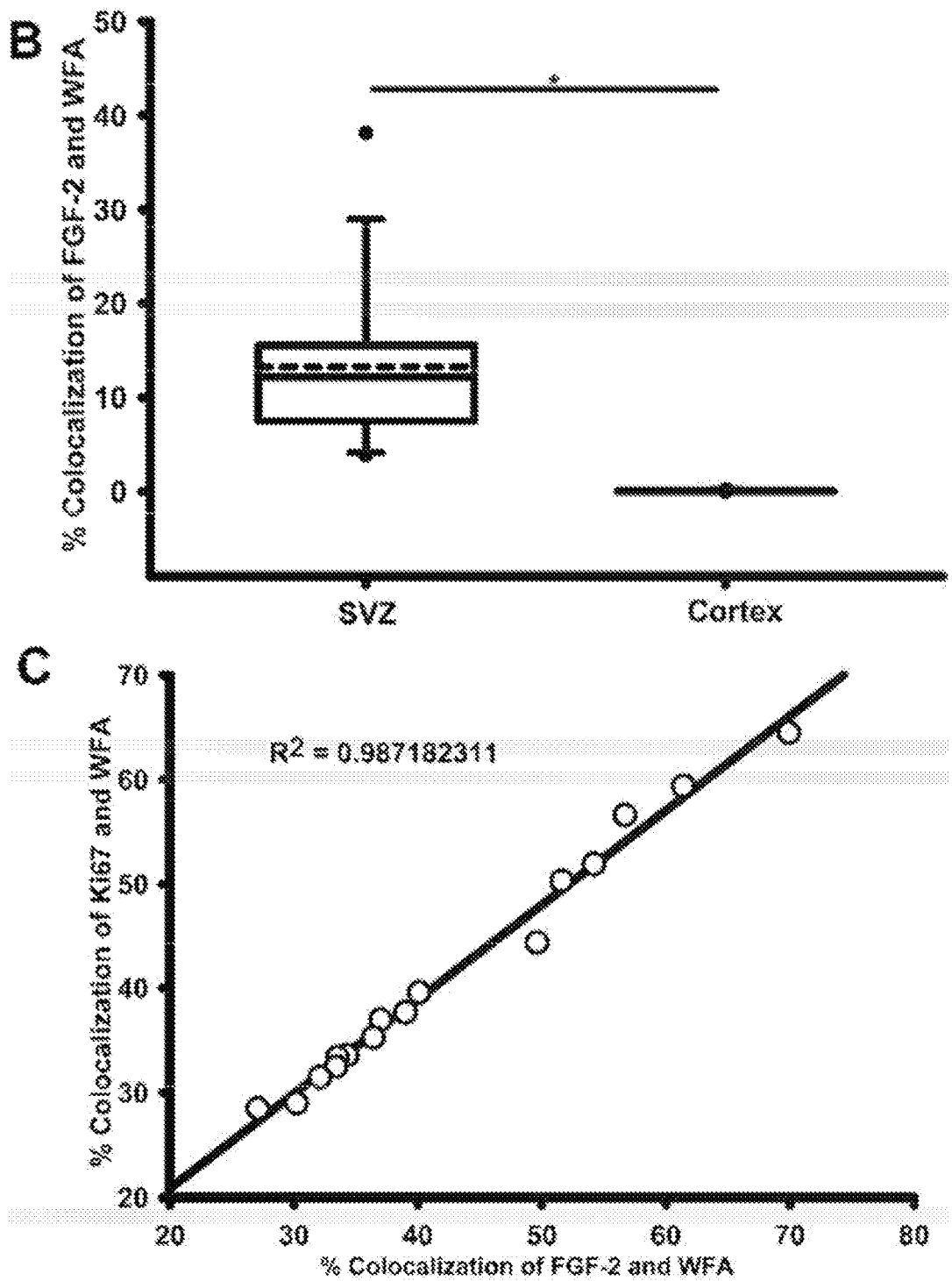

Because HA is a major unsulfated GAG present in the brain tissue ECM in addition to sulfated CS-GAGs, the extent of FGF2 binding to HA and CS-GAG matrices when presented in solution simultaneously to both matrices was investigated. HA and CS-GAG matrices were patterned as described in the methods above, and performed immunohistochemical analysis using fluorescein conjugated WFA lectin to label the CS-GAG matrix, and antibody labeling of FGF2 bound to CS-GAG and HA matrices as described above. Results from these assays qualitatively demonstrate the enhanced WFA+ staining of the CS-GAG matrix when compared to the HA matrix (FIGS. 12A and 12B). These results also demonstrate that FGF2 bound preferentially to the CS-GAG matrix when compared to HA matrix (FIGS. 12C and 12D). The colocalization of FGF2 with CS-GAGs is also evidenced in the adult rat SVZ (FIG. 13). When compared to the cortex, a significantly ($p < 0.001$) higher percentage colocalization of FGF2 was observed with WFA+ brain tissue in the SVZ (FIG. 13A). No significant differences were observed between the Ki67/WFA+ and FGF2/WFA+ tissue in the rat SVZ (FIG. 13B). A high correlation of Ki67/WFA+ tissue with FGF2/WFA+ tissue was observed in the rat SVZ (FIG. 13C).

CS-GAG Matrix Induced Neuroprotection of Brain Tissue 4 Weeks Post-TBI

To evaluate the extent of neural tissue loss 4 weeks post-TBI, cresyl violet staining of coronal brain tissue sections was performed. A qualitative comparison of neuronal presence in brain tissue indicated that TBI and NSC-only treated control animals experienced extensive neuronal loss as evidenced by the lack of neural tissue and Nissl staining in the region surrounding the impacted site (FIGS.

Figures 14A, 14B, 14C, 14D:
FIGS. 14A, 14B, 14C, 14D, and 14E show Nissl staining to demonstrate the extent of neuronal presence in coronal brain sections obtained 4 weeks post-TBI from (FIG. 14A) TBI only control.
Figure 14E:
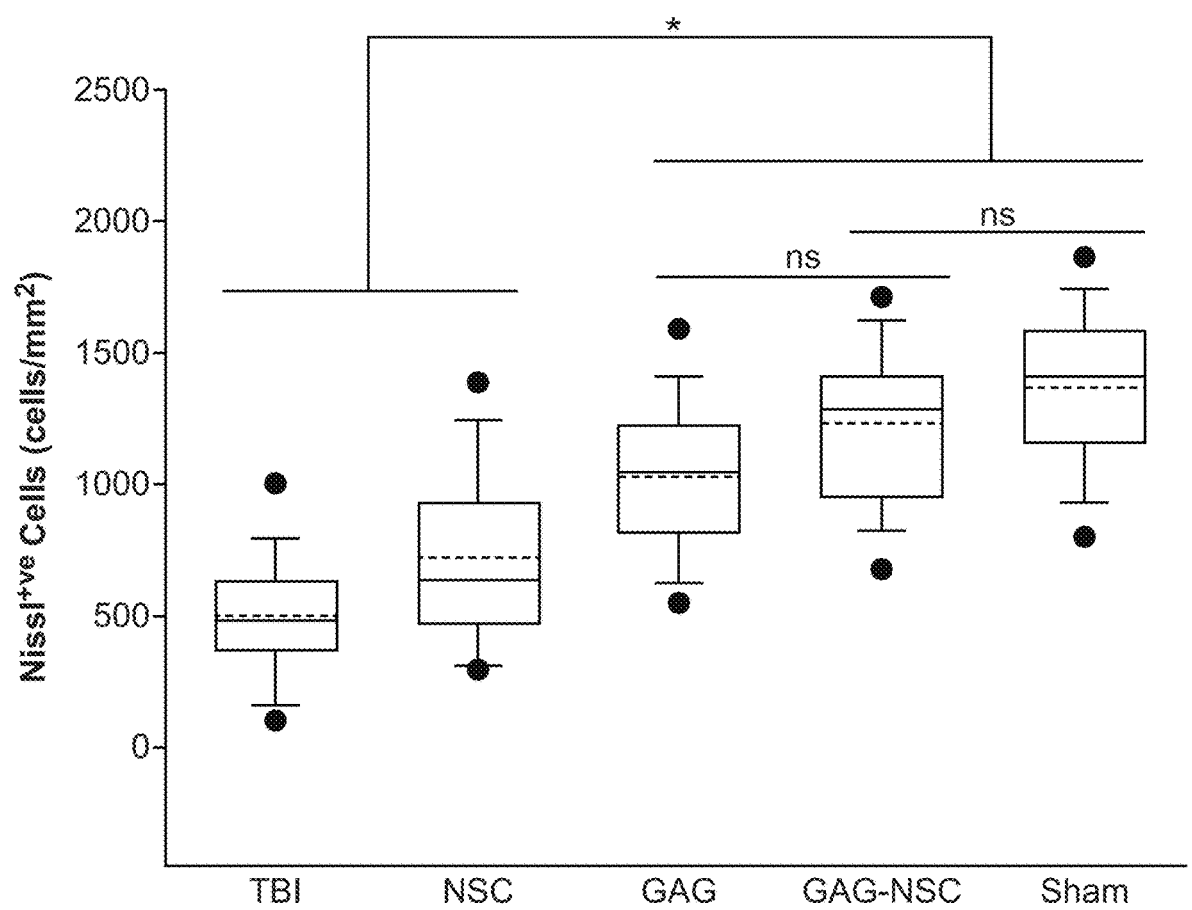

14A and 14B). In comparison, the GAG only and GAG-NSC treated animals demonstrated a healthy presence of neuronal tissue, as indicated by the significantly higher presence of cresyl violet labeled Nissl bodies in the region surrounding the CCI impact (FIGS. 14C and 14D), when compared to control TBI and NSC only treated animals. To quantify the extent of neuronal loss across these treatments, Nissl bodies were counted using methods presented above. The extent of neuronal loss in sham, NSC, GAG, and GAG-NSC treated animals were compared to the control TBI only treated animals. Results from these analyses demonstrate that the sham, GAG, and GAG-NSC groups have significantly ($p<0.05$) greater presence of neurons as indicated by positive Nissl staining when compared to TBI only treated animals (FIG. 14E). Pairwise multiple comparisons between all groups also indicate that both the GAG and GAG-NSC treated animals demonstrate significantly ($p<0.05$) greater neuronal presence as indicated by positive Nissl staining when compared to the control TBI only, and NSC only treated animals (FIG. 14E). The NSC treated animals showed significantly ($p<0.05$) lesser Nissl staining when compared to sham control. However, no significant differences in Nissl staining were observed between the sham, and GAG-NSC groups; and between the GAG and GAG-NSC groups.

Survival and Proliferation of NSCs Transplanted in CS-GAG Matrices 4 Weeks Post-TBI.

The survival and proliferation of PKH26GL-labeled allogenic rat NSCs delivered either alone or encapsulated in CS-GAG matrices was evaluated using immunohistochemical techniques as described above. The results demonstrate the significantly higher retention of NSCs in the lesion area when encapsulated and delivered in CS-GAG matrices when compared to NSCs delivered in basal media, as demonstrated by the significantly ($p<0.01$) greater colabeling of the cell-membrane dye PKH26GL with the NSC marker Sox1 4 weeks post-TBI (FIGS. 15A, 15B, and 15C). NSCs delivered in CS-GAG matrices also demonstrated a significantly ($p<0.01$) greater number of cells colabeled for PKH26GL and the cell proliferation marker Ki67 (FIGS. 15A, 15B, and 15D).

Local Retention of FGF2 and Maintenance of the Undifferentiated State of NSCs in CS-GAG Matrices 4 Weeks Post-TBI.

Figure 16A:
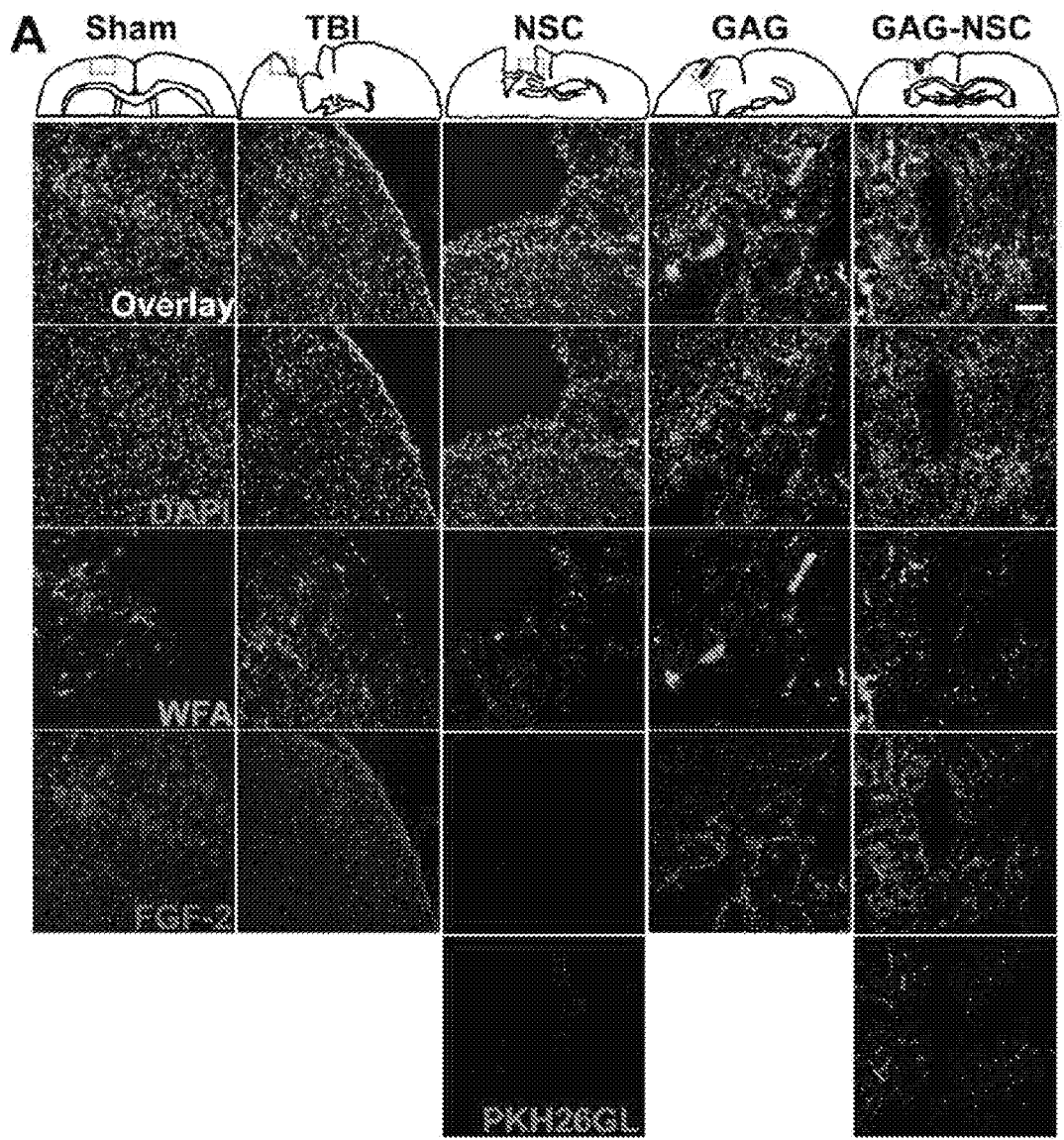
FIGS. 16A and 16B show FGF2 presence in brain tissue.
Figure 16B:
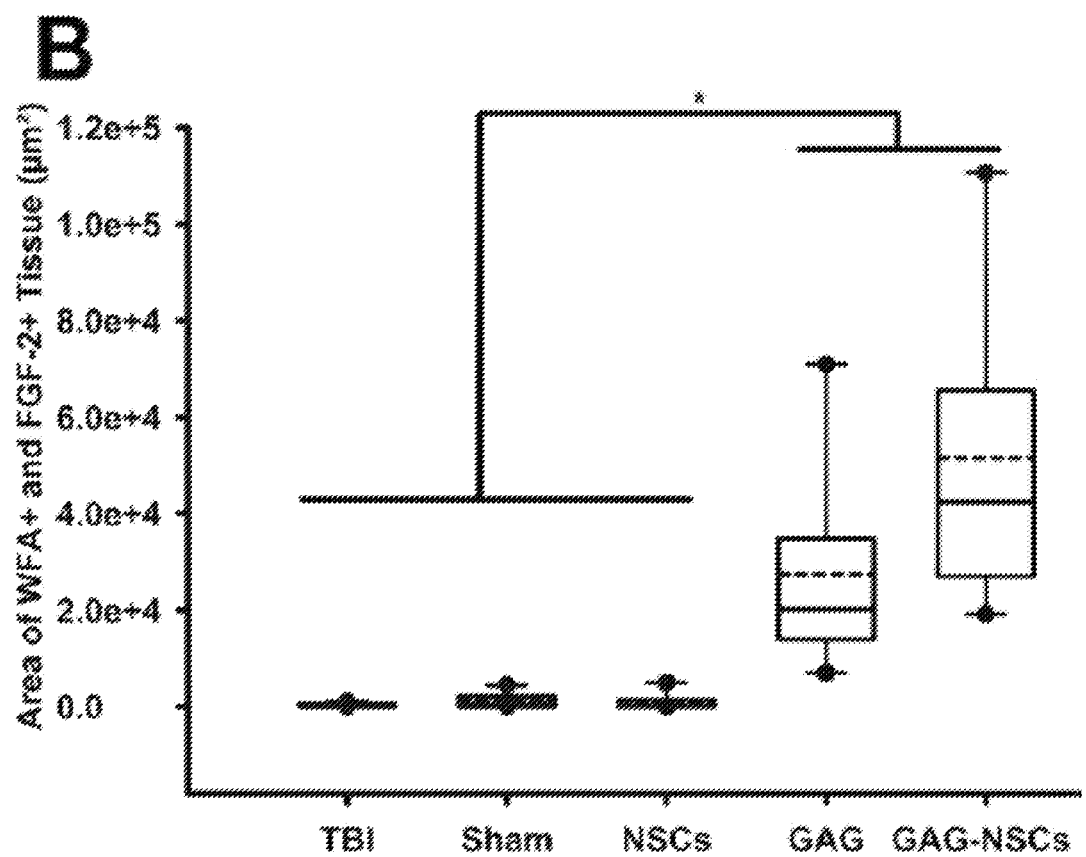
Figure 17A:
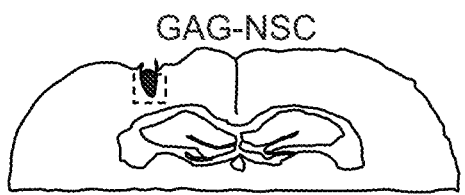
FIGS. 17A, 17B, 17C, and 17D show the differentiation of NSCs transplanted in CS-GAG matrices. Representative images of the region corresponding to the red dotted box surrounding the lesion area in coronal brain sections obtained from CS-GAG-NSC treated animals.
Figure 17B:
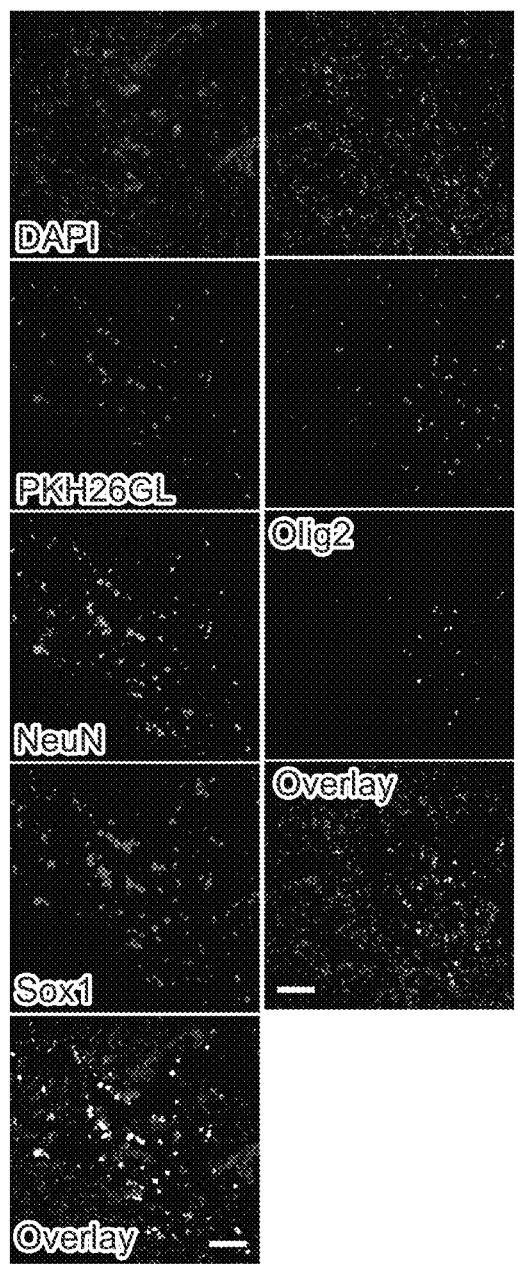
Figure 17C:
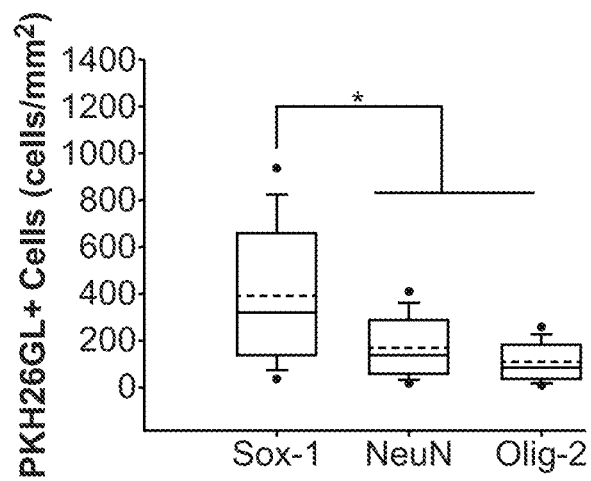
Figure 17D:
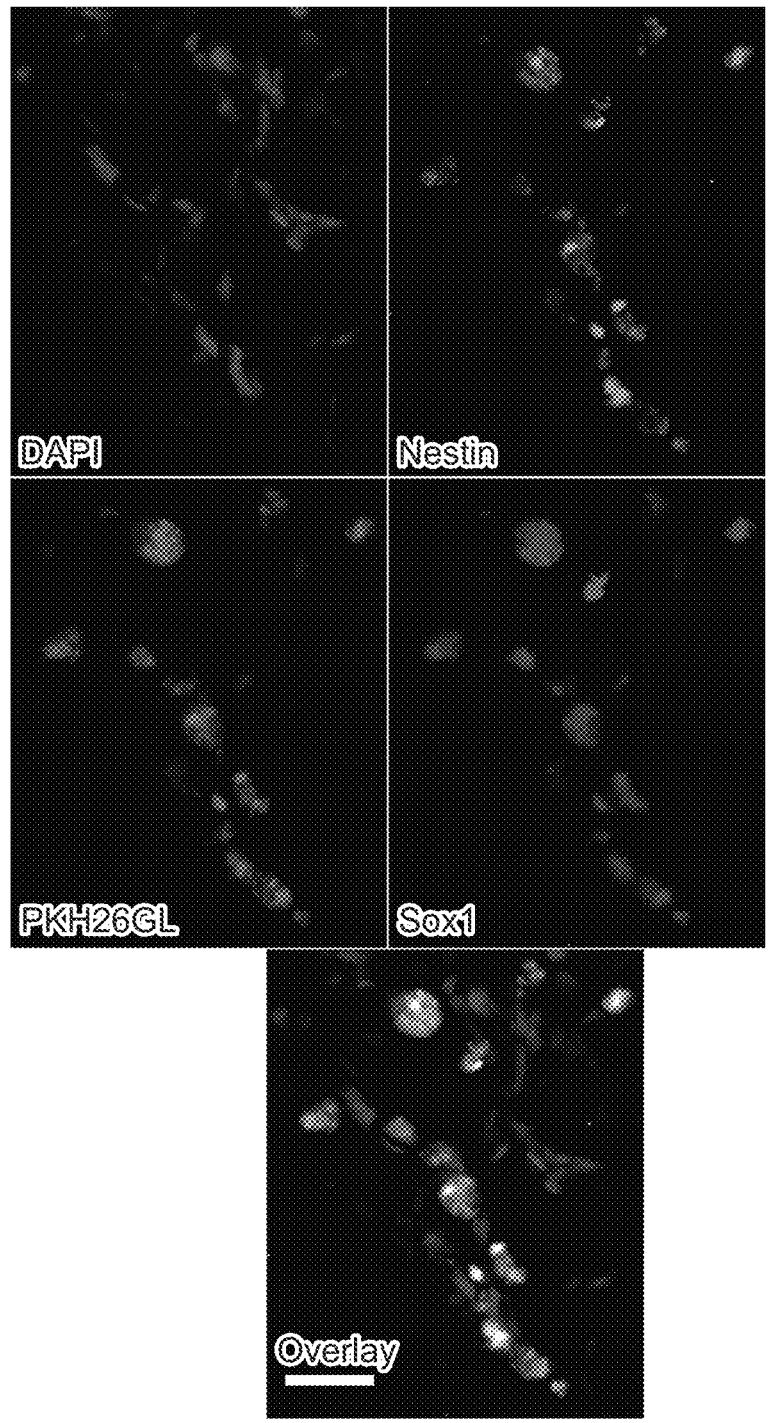

Quantitative immunohistochemical analysis of brain tissue 4 weeks post-TBI indicated that animals implanted with CS-GAG matrices alone, or with CS-GAG matrices carrying NSCs demonstrated significantly ($p<0.05$) controls, and NSC only treated animals (FIGS. 16A and 16B). A quantitative analysis of cell differentiation of transplanted cells indicated that a significantly high number of PKH26GL labeled cells expressed the NSC marker Sox1 when compared to the neuronal differentiation marker NeuN, and the oligodendrocyte marker Olig2 (FIGS. 17B and 17C). NeuN+ cells in GAG-NSC treated animals also demonstrated the complete absence of NF200 staining for neurofilaments typically present in the neuronal cytoskeleton of mature neurons. High-magnification images of transplanted NSCs indicated a high degree of colocalization of the cell membrane marker PKH26GL with the NSC markers Sox1 and nestin (FIG. 17D).

Inflammatory Response and Astroglial Scarring Mediated by Implanted Matrices.

Figure 18A:
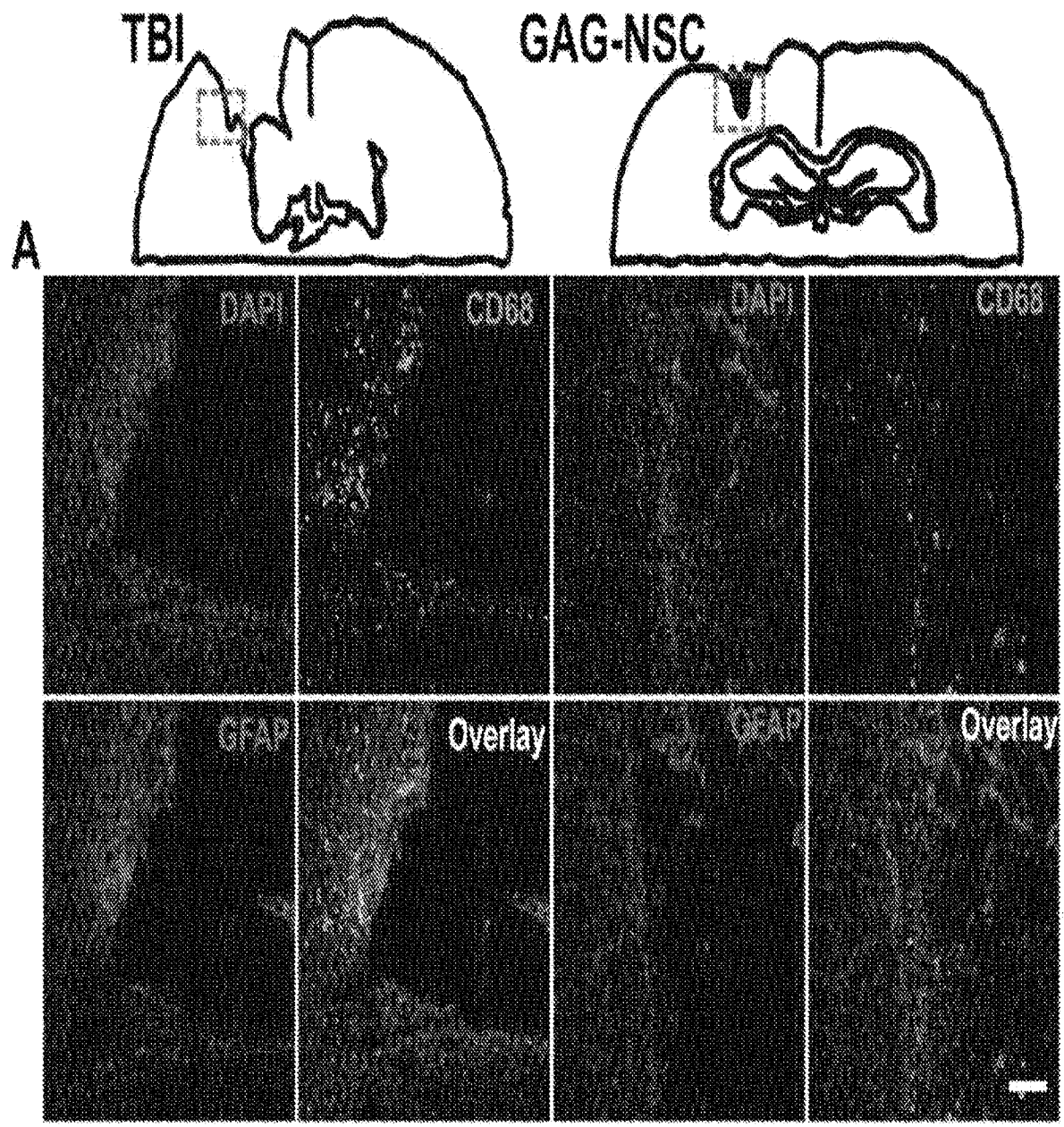
FIGS. 18A, 18B, and 18C show activated macrophage and reactive astrocyte presence surrounding the lesion site in TBI only control and CS-GAG-NSC treated animals.
Figures 18B, 18C:
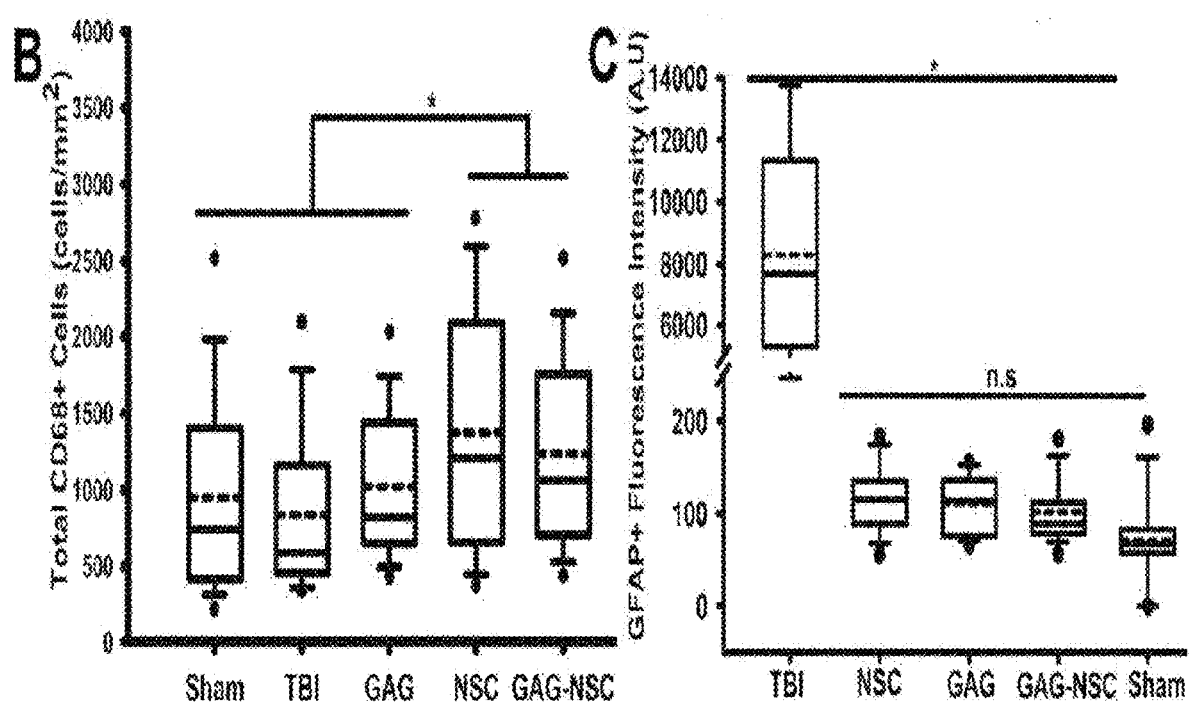

To assess the extent of inflammatory response and astroglial scarring mediated by CSGAG matrix implants 4 weeks post-TBI, immunohistochemical staining of coronal sections was performed using antibodies against GFAP for reactive astrocytes, and CD68 for activated macrophages. Due to the large extent of necrotic tissue loss observed in the brain tissue explanted from TBI-only control animals, the localization of CD68+ cells was confined to the lesion boundaries as depicted in FIG. 18A. In comparison, CD68+ cells were distributed throughout the matrix in the GAG-NSC treated group (FIG. 18A). A quantification of CD68+ cells in the brain tissue of CS-GAG matrix implanted animals showed a significant increase in cellular presence in the NSC and GAG-NSC treated animals when compared to sham, TBI, and GAG matrix treated animals (FIG. 18B). In contrast, the presence of reactive astrocytes was observed to be the highest in coronal sections obtained from the TBI-only control animals, as evaluated by the fluorescence intensity analysis when compared to all other treatments (FIG. 18C). There were no significant differences in GFAP fluorescence intensity observed between the treatment groups and the sham control animals (FIG. 18C). Interestingly, GFAP staining in the matrix treated animals was confined to the lesion boundary (FIG. 18A), and GFAP+ reactive astrocytes did not appear to infiltrate the matrix.

CONCLUSIONS

In summary, the results demonstrate that (a) sulfated CS-GAG matrices selectively bind and sequester FGF2 when compared to unsulfated HA matrices, and exhibit similar bioactive properties to native ECM in the SVZ; (b) when delivered intraparenchymally into the cortex of TBI impacted rats, CSGAG matrices promote neuroprotection and significantly enhance the survival and proliferation of transplanted NSCs 4 weeks post-TBI; (c) CS-GAG matrix implants promote FGF2 retention and promote the maintenance of the undifferentiated state of matrix encapsulated NSCs; and d) animals implanted with CS-GAG matrices induced a significantly attenuated inflammatory response, and reduced astroglial scarring response when compared to TBI control and NSC only treated animals. These results provide evidence to support the role of sulfated CS-GAGs in facilitating trophic factor signaling to promote NSC efficacy, and provide justification for their use as neuroprotective matrices that can be administered acutely to promote the repair and regeneration of brain tissue after a moderate-to-severe TBI.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating traumatic brain injury (TBI) in a subject, the method comprising administering a chondroitin sulfate glycosaminoglycan (CS-GAG) hydrogel to the subject at the site of the TBI, wherein the CS-GAG hydrogel does not comprise cells.

2. The method of claim 1 wherein the CS-GAG is sulfated.

3. The method of claim 1 wherein the CS-GAG is monosulfated or disulfonated.

4. The method of claim 1, wherein the CS-GAG hydrogel is selected from monosulfated chondroitin-4-sulfate (CS-A), chondroitin-6-sulfate (CS-C), disulfated chondroitin-4,6-sulfate (CS-E), or a combination thereof.

5. The method of claim 1, wherein the CS-GAG hydrogel comprises the addition of 2-aminoethyl methacrylate (AEMA) to the carboxylic acid groups on the glucuronic acid residues.

6. The method of claim 1 wherein the CS-GAG hydrogel is photopolymerized.

7. The method of claim 1 wherein the CS-GAG hydrogel is sterilized.

8. The method of claim 7, wherein the CS-GAG hydrogel is sterilized by gamma irradiation or ethylene oxide.

9. The method of claim 1, wherein the CS-GAG hydrogel further comprises a trophic factor, an adhesion molecule, an adhesion molecule receptor, or a combination thereof.

10. The method of claim 1, wherein the CS-GAG hydrogel is lyophilized and the method further comprises rehydrating the lyophilized CS-GAG hydrogel prior to administration.

11. The method of claim 10, wherein the CS-GAG hydrogel is rehydrated with a rehydration solution comprising a trophic factor, an adhesion molecule, an adhesion molecule receptor, or a combination thereof.

12. The method of claim 11, wherein the trophic factor is selected from FGF-2, BDNF, EGF, IL10, or a combination thereof.

13. The method of claim 11, wherein the adhesion molecule or adhesion molecule receptor is selected form CXCR4, CXCR7, FAK, or a combination thereof.

14. The method of claim 1, wherein the CS-GAG hydrogel is administered at the site of the TBI by direct injection.

15. The method of claim 1, wherein the CS-GAG hydrogel is administered by intraparenchymal injection.

16. The method of claim 1, wherein the subject demonstrates reduced inflammation and/or reduced astroglial scarring at the site of the TBI.

17. The method of claim 1, preventing neuronal cell loss at the site of the TBI.

18. The method of claim 1, stimulating the regeneration of injured brain tissue at the TBI.

* * * * *